(12) United States Patent
Williams et al.

(10) Patent No.: US 9,724,416 B2
(45) Date of Patent: Aug. 8, 2017

(54) COMPOSITION FOR IMPROVING OR PROMOTING HAIR GROWTH CONTAINING, AS ACTIVE INGREDIENTS, PHOTOSENSITIZER IRRADIATED WITH LIGHT AND PEPTIDE, AND METHOD USING SAME

(71) Applicant: GWANGJU INSTITUTE OF SCIENCE AND TECHNOLOGY, Gwangju (KR)

(72) Inventors: Darren Williams, Gwangju (KR); Da-Woon Jung, Gwangju (KR); Soon-Ho Yim, Gwangju (KR)

(73) Assignee: UNIQUE MEDICARE CO., LTD., Gwangju (KR)

( * ) Notice: Subject to any disclaimer, the term of this patent is extended or adjusted under 35 U.S.C. 154(b) by 186 days.

(21) Appl. No.: 14/401,773

(22) PCT Filed: May 8, 2013

(86) PCT No.: PCT/KR2013/004036
§ 371 (c)(1),
(2) Date: Nov. 17, 2014

(87) PCT Pub. No.: WO2013/172586
PCT Pub. Date: Nov. 21, 2013

(65) Prior Publication Data
US 2015/0140139 A1 May 21, 2015

(30) Foreign Application Priority Data
May 17, 2012 (KR) ........................ 10-2012-0052403

(51) Int. Cl.
| A61K 38/06 | (2006.01) |
| A61K 41/00 | (2006.01) |
| A61K 36/344 | (2006.01) |
| A61K 36/539 | (2006.01) |
| A61K 36/71 | (2006.01) |
| A61K 47/48 | (2006.01) |
| A61K 8/41 | (2006.01) |
| A61K 8/64 | (2006.01) |
| A61Q 7/00 | (2006.01) |

(52) U.S. Cl.
CPC ............ *A61K 41/0061* (2013.01); *A61K 8/41* (2013.01); *A61K 8/64* (2013.01); *A61K 36/344* (2013.01); *A61K 36/539* (2013.01); *A61K 36/71* (2013.01); *A61K 38/06* (2013.01); *A61K 47/48038* (2013.01); *A61Q 7/00* (2013.01); *A61K 2800/57* (2013.01); *A61K 2800/81* (2013.01)

(58) Field of Classification Search
None
See application file for complete search history.

(56) References Cited

U.S. PATENT DOCUMENTS

| 5,800,479 A | 9/1998 | Thiberg |
| 5,952,329 A | 9/1999 | Cincotta et al. |
| 5,965,598 A | 10/1999 | Roncucci et al. |
| 6,036,941 A | 3/2000 | Bottiroli et al. |
| 6,107,466 A | 8/2000 | Hasan et al. |
| 6,136,841 A | 10/2000 | Platzek et al. |
| 6,225,333 B1 | 5/2001 | Rodgers et al. |
| 7,268,155 B2 * | 9/2007 | Hasan ............... A61K 41/0019 424/9.6 |

FOREIGN PATENT DOCUMENTS

| KR | 10-2003-0057317 | 7/2003 |
| KR | 10-2006-0088129 | 8/2006 |
| KR | 10-2007-0010963 | 1/2007 |

(Continued)

OTHER PUBLICATIONS

Spangler,C.W., et al "Optimization of targeted two-photon PDT triads for the treatment of head and neck cancers" Photonic Therapeutics and Diagnostics VIII, (ed.Nikiforos Kollias, et al), Proc. of SPIE, vol. 8207 (Jan 21, 2012; published Feb. 3, 2012), 820720, pp. 1-8. doi: 10.1117/12.909640.*

Vladimir A. Botchkarev, "Stress and the Hair Follicle: Exploring the Connections", American Journal of Pathology, vol. 162, No. 3, Mar. 2003, pp. 709-712.

Kwang Ho Yoo, et al., "Photodynamic Therapy with Methyl 5-Aminolevulinate Acid Might be Ineffective in Recalcitrant Alopecia Totalis regardless of Using a Microneedle Roller to Increase Skin Penetration", Dermatologic Surgery, 2010 36 (5), pp. 618-622.

Yuki Morokuma et al., "Hair growth stimulatory effect by a combination of 5-aminolevulinic acid and iron ion", International Journal of Dermatology, 2008, 47 (12) pp. 1298-1303.

Threes G.M. Smijs et al., "The Susceptibility of Dermatophytes to Photodynamic Treatment with Special Focus on Trichophyton rubrum", Photochemistry and Photobiology, 2011, 87 pp. 2-13.

International Search Report for International Application No. PCT/KR2013/004036, dated Sep. 17, 2013.

(Continued)

*Primary Examiner* — Thomas S Heard
(74) *Attorney, Agent, or Firm* — Kile Park Reed & Houtteman PLLC

(57) ABSTRACT

The present invention relates to a composition for improving or promoting hair growth, which contains, as an active ingredient, a photosensitizer-peptide conjugate, and to a method for screening for the hair growth promoter using the active ingredients. ALA, which is the photosensitizer of the present invention, is preferably activated by LED radiation, and more preferably activated by radiation having a long wavelength of 650 to 675 nm. The peptide of the present invention is a peptide in which 3 to 7 amino acid residues are incorporated (most preferably, glycine-histidine-lysine), and may cooperate with the photosensitizer to enable very superior hair growth improving or promoting effects using light radiation. Further, the composition of the present invention may exhibit further superior effects when natural extracts (for example, *Cimicifuga heracleifolia* extracts, *Scutellaria baicalensis* extracts or *Codonopsis lanceolata* extracts) are added. Thus, the composition of the present invention can be significantly advantageously applied to drugs, quasi-drugs, and cosmetics.

3 Claims, 27 Drawing Sheets

(56) References Cited

FOREIGN PATENT DOCUMENTS

KR    10-2008-0012813      2/2008
KR    10-2010-0116882      11/2010

OTHER PUBLICATIONS

R. B. Merrifield, "Solid Phase Peptide Synthesis. I. The Synthesis of a Tetrapeptide", Journal of American Chemical Society, vol. 85, Jul. 20, 1963, pp. 2149-2154.
Stewart, et al., "Solid Phase Peptide Synthesis", 2nd. ed., Pierce Chem. Co.: Rockford, pp. 110-111(1984).
Calzavara-Pinton Piergiacomo et al., "A Critical Reappraisal of Off-Label Indications for Topical Photodynamic Therapy with Aminolevulinic Acid and Methylaminolevulinate", Reviews on Recent Clinical Trials, 2010, 5 pages 112-116.

\* cited by examiner

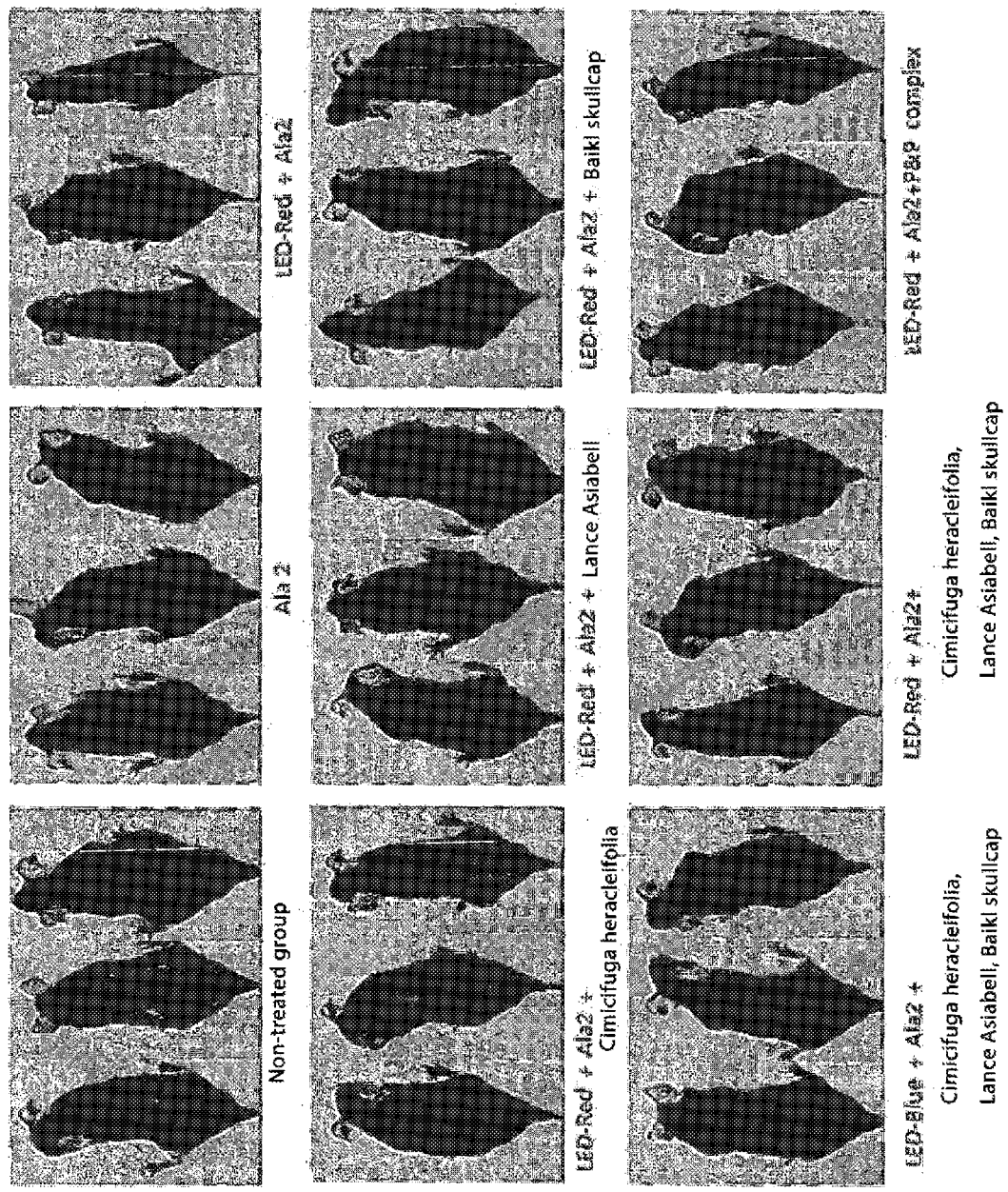

COMPOSITION FOR IMPROVING OR PROMOTING HAIR GROWTH CONTAINING, AS ACTIVE INGREDIENTS, PHOTOSENSITIZER IRRADIATED WITH LIGHT AND PEPTIDE, AND METHOD USING SAME

TECHNICAL FIELD

This application claims the benefit of and priority to Korean Patent Application No. 10-2012-0052403, filed May 17, 2012 to the Korean Intellectual Property Office. The content of the foregoing application is incorporated herein by reference in its entirety.

The present invention relates to a composition for improving or promoting hair growth containing, as active ingredients, a photosensitizer irradiated with light and a peptide, and a method using the same.

BACKGROUND ART

Alopecia or a hair thinning symptom has been gradually increased due to industrial development and environmental pollution, stress, and an increasingly aging population, and with the advent of the era of well-being, interest in the quality of life and appearance has increased. Alopecia which means hair loss at the scalp is caused by several factors that, for example, include (a) internal factors such as a genetic constitution and an action of male hormones; (b) mental stress in daily life; and (c) external factors such as the accumulation of lipoperoxide in the scalp. It is known that a hair loss symptom is caused by a very complicated process.

Human hair is subjected to a process of hair loss and regeneration while anagen, catagen and telogen are repeated periodically, and the hair cycle is done through hormonal regulation and regulation of many growth factors. The hair is buried in the skin of approximately 3 to 5 mm to be accumulated in the epidermis and the dermis, and this portion is called a hair follicle. There is a dermal papilla that is a formation dominating the hair over this hair follicle, there is a germinal matrix that produces the hair above the dermal papilla, the germinal matrix produces a new hair and pushes up it while continuing to divide. The dermal papilla cells have the cycle of anagen in which growth is proceeding actively, catagen in which regression begins, and telogen, and if the dermal papilla cells receive signals from the adjacent cells after telogen, they are entering anagen again, in which regeneration of the cells is carried out, resulting in the generation of a new hair. Meanwhile, due to severe stress or nutrient deficiency, the hair is entering telogen through early catagen, resulting in the introduction of a severe hair loss symptom (American Journal of Pathology, Vol, 162. No. 3, Stress and the Hair Follicle: Exploring the Connections (2003)).

In recent years, hair loss in the younger generation including obesity-related hair loss of females as well as male pattern hair loss has been gradually spreading. In order to improve such a hair loss phenomenon, many types of hair growth solutions or hair restorers have been commercially available.

In the case of currently commercially available hair growth solutions or hair restorers (e.g., minoxidil, finasteride), since these exhibit a side effect problem according to an application of hormonal drugs or have an effect only on the part in which the hair roots have been activated, although these have an effect on prevention of hair loss, these are less effective, or have an effect only if continuing to ingest or apply these, on growth of hair (i.e., hair restoration) which is in the telogen state for the long-term. There is a need for an economic and stable technical development in order to solve alopecia or a hair thinning symptom.

The main ingredients used in currently commercially available hair growth solutions or hair restorers include a vasodilator containing, as main ingredients, capronium chloride, minoxidil and extracts of various plants, for circulating sufficient blood in the scalp, female hormones such as estrogen, estradiol, and progesterone, for inhibiting the action of male hormones which are attached to the dermal papilla to eliminate the hair, or a male hormone activation inhibitor such as pentadecanoic acid and finasteride.

However, although most of these hair growth solutions and hair restorers are somewhat effective in prevention of hair loss, it is known that their effects related to hair restoration are not satisfactory. That is, since these formulations have mostly an effect on the part in which the hair roots have been activated, these are less effective on growth of hair (i.e., hair restoration) which is in the telogen state for the long-term. It is known that these formulations are less effective on the scalp of thin hair in which hair loss has been progressed and the hair follicle has been shrinked.

Besides, cosmetics products have utilized extracts of plants which are inexpensive but are less effective, and thus they have a marginal effect.

Treatment and solution for hair loss have changed considerably over a long period of time. Wigs, toupees and hair enlargement can hide a bald patch, but do not cause a new growth. Two available drugs known so far (minoxidil and finasteride) can delay additional hair loss, but actually, have no role in inducing regeneration of a new hair follicle. Also, among many hair cosmetics, many hair loss prevention products using plant extracts and so on were launched. In particular, products containing extracts such as *sophora*, pepper, Swertia herb, Moms *alba* L., mulberry leaf, *ginseng*, licorice, peony, *Rehmannia glutinosa*, fennel anise, *Cornus* fruit, and garlic; products produced by adding compositions containing xanthine and growth hormones, by which restraint of cell metabolism according to an excess of dihydrotestosterone (DHT) is improved, and at the same time the growth hormones promote hair growth, thus preventing hair loss and regenerating hair to exhibit the hair growth promoting effect; products for promoting hair growth which contain minerals and vitamins, green tea, rosemary, wormwood, and licorice extracts for promoting hair restoration and growth of hair, and which nourish the scalp and hair and are effective in preventing hair loss and promoting hair growth; and products for preventing male pattern hair loss, produced by mixing substance such as vitamin B, vitamin C, vitamin D, vitamin E, nicotinic acid, pantothenic acid, biotin and folic acid, and plant extracts, by which 5-alpha reductase is inhibited in the human body so that dihydrotestosterone is not formed in the metabolic process of male hormones and which help the metabolism of hair were developed. However, products having an effect on generation of de novo hair are difficult to find.

As currently commercially available hair growth solutions or hair restorers, since these exhibit a side effect problem according to an application of hormonal drugs or have an effect only on the part in which the hair roots have been activated, although these have an effect on prevention of hair loss, these are less effective, or have an effect only if continuing to ingest or apply these, on growth of hair (i.e., hair restoration) which is in the telogen state over a long period of time. There is a need for an economical and stable technical development in order to solve alopecia or hair thinning symptom.

A number of papers and patent documents are referenced and their citations are indicated throughout this specification. The contents of the cited papers and patent documents are incorporated herein by reference in their entirety, so the level of the technical field to which the invention pertains and the contents of the present invention are more clearly described.

DISCLOSURE

Technical Problem

The present inventors have tried to develop a substance capable of very effectively promoting the growth of hair without side effects. As a result, the present inventors have confirmed that a peptide (preferably, a GHK peptide) coupled to a photosensitizer [preferably, 5-aminolevulinic acid (ALA)] is activated by LED radiation having a long wavelength (preferably, from 650 to 675 nm) to promote the growth of hair significantly, and further, when it is treated along with *Cimicifuga heracleifolia* extracts, Baikl skullcap extracts or Lance Asiabell extracts, it exhibits more superior hair growth promoting effects, thereby completing the present invention.

Therefore, the present invention is directed to providing a composition for improving or promoting hair growth.

Also, the present invention is directed to providing a method for screening for a hair growth promoter.

Moreover, the present invention is directed to providing a method for improving or promoting hair growth.

Other objects and advantages of the present invention will be made clearer by the following detailed description of the invention, claims and drawings.

Technical Solution

One aspect of the present invention provides a composition for improving or promoting hair growth, which contains, as an active ingredient, a peptide coupled to a photosensitizer (photosensitizer-peptide).

The present inventors have tried to develop a substance capable of very effectively promoting the growth of hair without side effects. As a result, The present inventors have confirmed that a peptide (preferably, GHK peptide) coupled to a photosensitizer [preferably, 5-aminolevulinic acid (ALA)] is activated by LED radiation having a long wavelength (preferably, from 650 to 675 nm) to promote the growth of hair significantly, and further, when it is treated along with *Cimicifuga heracleifolia* extracts, Baikl skullcap extracts or Lance Asiabell extracts, it exhibits more superior hair growth promoting effects, thereby completing the present invention.

Photodynamic therapy (PDT) is a therapy that is being developed, is used mainly for the treatment of cancer, and is also used for infection, the treatment of wounds and, non-malignant diseases including a variety of dermatological diseases. PDT is based on the interaction of a particular photosensitizer with oxygen and light. According to clinical results, PDT has an advantage over other therapies for the treatment of some pathological conditions, and is effective on the keratin fibers of acne and a variety of skin cancers. General information on clinical use of PDT is described in U.S. Pat. No. 6,225,333, U.S. Pat. No. 6,136,841, U.S. Pat. No. 6,107,466, U.S. Pat. No. 6,036,941, U.S. Pat. No. 5,965,598, and U.S. Pat. No. 5,952,329, the contents of which are incorporated herein by reference in their entirety. Also, for a safe and effective PDT, a light source is important. The light source should have the following characteristics: (a) a high light intensity (i.e., a high radiation flux); (b) easy light dose; (c) a peak wavelength of emission spectrum; (d) a uniform intensity of radiation; (e) low-priced operating costs; and (f) a simple structure.

According to the present invention, the present invention has employed a peptide conjugate coupled to a photosensitizer (photosensitizer-peptide) for improving or promoting hair growth.

According to a preferred embodiment of the present invention, the photosensitizer of the present invention is activated in accordance with the exposure to a wavelength of a particular region, and may be used effectively together with pine resin extracts for the treatment of periodontal disease. Compared to the above-described conventional art (e.g., chemotherapy using antibiotics), the photosensitizer of the present invention has the following advantages: (a) efficient treatment effects by activation using light radiation; (b) long-term availability; (c) an absence of cytotoxicity; (d) a low treatment concentration; and (e) targeting of a specific bacteria using modifications (e.g., physical or chemical modifications).

According to a preferred embodiment of the present invention, the photosensitizer of the present invention includes 5-aminolevulinic acid (ALA), an ALA derivative, and a porphyrin derivative, more preferably, ALA, 5-ALA-induced protoporphyrin IX, hematophorphyrin (HpD), Photogem, tin etiopurpurin (SnET2), mono-1-aspartyl chlorin e6 (NPe6), a benzoporphyrin derivative (BPD), meso-tetra-(hydroxyphenyl) chlorin (mTHPC), radachlorin, aluminum tetrasulfophthalocyanine (ALPcS4), or meso-tetra(sulphonatophenyl)porphine (TPPS), most preferably, ALA.

ALA, which is the photosensitizer used in the present invention, is an aliphatic compound having 5 carbon atoms, and is an essential precursor of the biosynthesis process of all tetrapyrroles including chlorophyll and heme in a living body, and the tetrapyrroles are biosynthesized to become hemoglobin, chlorophyll, and heme with a coenzyme such as vitamin B12 through several steps in the living body, and are represented by the following Chemical formula 1:

[Chemical formula 1]

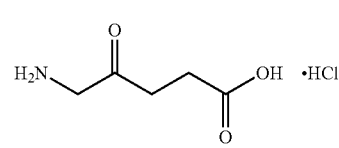

Depending on the characteristics of a biosynthetic pathway of ALA, it can be applied to agricultural applications such as plant growth promoters, herbicides, or insecticides, to medical applications such as anticancer agents and brain tumor diagnoses, and to engineering applications such as the production of enzymes including cosmetic additives or a heme structure. ALA is an environmentally friendly biotic pesticide and plant growth promoter, and when treated to plants, the growth and development of plants are regulated. When treating with a low concentration of ALA, in crops such as radishes, kidney beans, barley, potatoes, garlic, rice, corn, etc., the treated group is growth-promoted by 10 to 60% better than a non-treated group. It was reported that this promoting effect was caused by an increase in chlorophyll content, an increase in photosynthetic activity, and respiration inhibition.

In the medical field, ALA has been already used as biological active materials such as antimicrobial resistance drugs and a skin cancer treatment drug. Thus, ALA is widely known as a photosensitizer of photodynamic therapy (PDT) for malignant tumor treatment accepted by the FDA.

ALA forms a photosensitizer, protoporphyrin IX which is a precursor through a biosynthetic pathway of heme, and is metabolized rapidly after showing activity for a short time. When protoporphyrin IX starts to be activated as a photosensitizer, it shows fluorescence and shows cytotoxicity. Utilizing this, it is used for purposes of the diagnosis or treatment of cancer.

For ALA used in the present invention, that produced by the above-described various methods may be used. For example, the ALA ingredient can be obtained by proceeding the synthesis studies using sugar fermentation, separation and purification methods and a catalyst reaction for corn extracts containing germ cells, but is not limited to these.

As the light source of PDT which may be used in the present invention, infrared pulse light and visible light are irradiated for 1 to 3 minutes, preferably, light having a wavelength of 660 nm in the region of the visible light is used (see U.S. Pat. No. 5,800,479). Also, a source well known in the relevant art may be used as the light source, and for example, there are light-emitting diodes (LEDs), filtered white light sources [e.g., a white lamp, intense pulsed light (IPL), a fluorescent tube, etc.], low-intensity narrow or wide discharge tubes and so on.

A copper-peptide (Cu-GHK) used in the present invention is a substance present in the human body in which copper is chelated to glycyl-histidyl-lysine (GHK). A copper-peptide function as the growth factor of skin cells, primarily protects the tissue, and prevents inflammation due to tissue damage. Also, copper-peptide acts as a signal of skin tissue regeneration for regenerating a damaged protein and replacing the damaged tissue with normal tissue. That is, when a tissue has been damaged, a copper-peptide may be referred to as a feedback signal which performs the healing and regeneration in the tissue and protects the tissue. The known functions of a copper-peptide are as follows: (a) an increase in skin metalloproteinases activities; (b) wrinkle improvement, an increase in the biosynthesis of collagen and elastin; (c) damage prevention in the tissue, an increase in the generation of proteoglycans and glycosaminoglycans; (d) anti-aging, a function which activates superoxide dismutases of the skin, and detoxifies free radicals in water layer of the skin to increase the skin activity; (e) improvement of the damaged skin, a function which newly repairs and tightens the stratum corneum for protecting the skin; and (f) prevention of hair loss.

The copper-peptide is a combination of copper and a peptide, and is effective for the regeneration of skin and regeneration of hair in the hair follicle. An increase in the size of the hair follicle and hair growth rate due to the administration of the copper-peptide occurs by supplying the hair follicle with proper nutrition through a change in blood flow so that hair with thick hair shafts grows rapidly. As an example of the copper-peptide, the copper-peptide (Cu-GHK), in which copper is coupled to glycyl-histidyl-lysine (GHK) which is a very rare series extracted from proteins in the human body, exists in a vigorous state when combined from proteins such as collagen, thrombospondin, a fibrin α-chain, prokininogen, a complement C1q, interleukin 4, skin collagenase, coagulation factor XI and sparc, primarily protects the tissue, and prevents inflammation due to the tissue damage. Also, it acts as a signal of tissue reconstruction for regenerating a damaged protein and replacing the damaged tissue with normal tissue. That is, when a tissue has been damaged, the Cu-GHK may be referred to as a feedback signal which performs the healing and regeneration in the tissue and protects the tissue. Moreover, since the Cu-GHK has an excellent ability to regenerate skin, the Cu-GHK promotes wound healing, enhances skin elasticity, and increases the subcutaneous fat layer to reverse the aging of the skin. Also, by increasing the success rate of skin graft surgery, the Cu-GHK is recognized as a superior material in dermatology. GHK analogs increase the size of the hair follicle with residual fat to promote hair growth and decrease hair loss.

According to a preferred embodiment of the present invention, the photosensitizer-peptide conjugate (for example, an ALA-peptide) of the present invention is a compound coupled via a covalent bond, and is represented by the following Chemical formulas 2 and 3:

[Chemical formula 2]

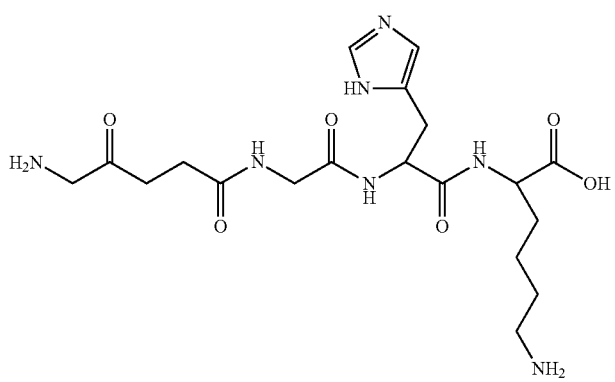

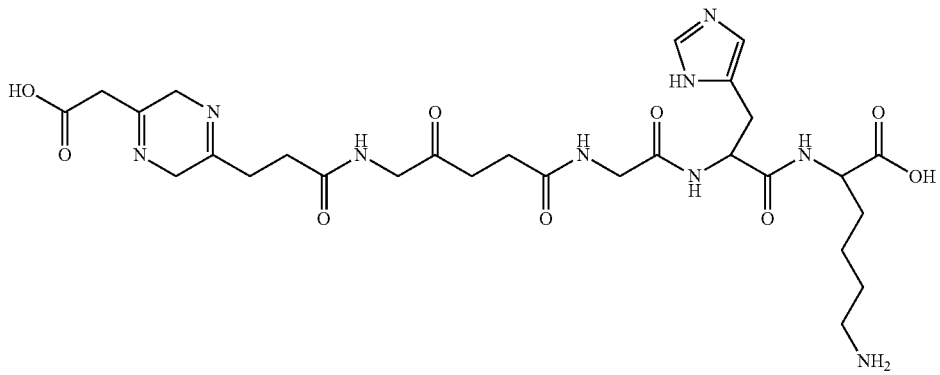

[Chemical formula 2]

The Chemical formula 3 represents a compound in which the dimerization of ALA occurs.

According to a preferred embodiment of the present invention, the photosensitizer-peptide conjugate of the present invention includes a peptide that is coupled to a hydroxyl group (—OH) of ALA represented by the Chemical formula 1.

According to a preferred embodiment of the present invention, the peptide is a peptide in which, identical or different, 3 to 7 amino acid residues selected from the group consisting of alanine, glycine, lysine, histidine, serine, proline, hydroxyproline, threonine, arginine, glutamine, methionine and glutamic acid, are amide-bonded. More preferably, the peptide is a peptide in which 3 to 5 amino acid residues are bonded (for example, glycine-lysine-histidine, glycine-histidine-lysine, glycine-proline-hydroxyproline, alanine-lysine-histidine, alanine-histidine-lysine, lysine-histidine-lysine, lysine-arginine-lysine, or lysine-threonine-threonine-lysine-serine). Even more preferably, the peptide is a peptide in which 3 to 4 amino acid residues are bonded. Most preferably, the peptide is a peptide in which 3 amino acid residues are bonded (for example, glycine-histidine-lysine).

The term "peptide" used herein denotes a linear molecule in which amino acid residues are bonded together by peptide bond. The peptide of the present invention may be produced according to a chemical synthesis method known in the relevant art, especially, solid-phase synthesis techniques (Merrifield, *J. Amer. Chem. Soc.* 85:2149-54(1963); Stewart, et al., *Solid Phase Peptide Synthesis,* 2nd. ed., Pierce Chem. Co.: Rockford, 111(1984)).

Preferably, a protecting group selected from the group consisting of an acetyl group, a fluorenyl methoxy carbonyl group, a formyl group, a palmitoyl group, a myristyl group, a stearyl group and polyethylene glycol (PEG) may be bonded to a terminal of the peptide. This modification may provide the peptide having a higher stability than that of a naturally occurring peptide.

This modification of the amino acid acts to significantly improve the stability of the peptide of the present invention. The term "stability" used herein denotes "in vivo" stability as well as storage stability (e.g., room temperature storage stability). Also, the protecting group acts to protect the peptide of the present invention from attacks by protein cleavage enzymes in a living body According to a preferred embodiment of the present invention, the photosensitizer-peptide conjugate of the present invention further enhances the activity of the peptide in the conjugate by activation of the photosensitizer using light radiation.

The term "photosensitizer-peptide conjugate" used herein denotes an unknown material that is used to examine whether or not the improvement or promotion of hair growth is caused by light irradiation.

The photosensitizer-peptide conjugate of the present invention using light irradiation (preferably, LED radiation) exhibits more superior hair growth improving or promoting effects (about a three- to four-fold increase) compared to a photosensitizer-peptide conjugate which is not irradiated with light (see FIGS. 6B and 20B). It means that the photosensitizer and the peptide activated by light irradiation exert synergistic effects with each other.

According to a preferred embodiment of the present invention, the photosensitizer-peptide conjugate used as an active ingredient of the present invention ranges from 1 to 1,000 mg/ml, more preferably from 10 to 500 mg/ml, even more preferably from 25 to 250 mg/ml, and most preferably from 50 to 150 mg/ml.

Meanwhile, the composition of the present invention may exhibit further superior hair growth promoting effects through the additional treatment of natural extracts. According to a preferred embodiment of the present invention, the composition of the present invention further includes various natural extracts, more preferably *Cimicifuga heracleifolia* extracts, Baikl skullcap extracts, or Lance Asiabell extracts, most preferably, Lance Asiabell extracts.

According to a preferred embodiment of the present invention, when treated along with the above-described natural extracts, the photosensitizer-peptide conjugate of the present invention using light irradiation (preferably, LED radiation) exhibits about a six-fold or more increase of more superior hair growth improving or promoting effects compared to a case of treatment with only a photosensitizer-peptide conjugate without light irradiation, and exhibits about a two-fold increase of hair growth improving or promoting effects compared to a photosensitizer-peptide conjugate which is irradiated with light (see FIG. 20B). It means that the above-described natural extracts further promote the effects of the photosensitizer and the peptide activated by light irradiation.

*Cimicifuga heracleifolia* is a flowering plant body belonging to Ranuncellaceae family, is pith consisting of 12 to 18 species, grows naturally in the temperate regions of the Northern Hemisphere. The dried rhizome and root of most *Cimicifuga heracleifolia* species have been widely used as an herbal dietary supplement. The root of *Cimicifuga heracleifolia* is generally picked in the fall, and freshly or after being dried, is used as an analgesic, an antibacterial agent, an antiviral agent, an antipyretic drug and a sedative.

Baikl skullcap (*Scutellaria baicalensis*) is a perennial grass belonging to Lamiaceae, grows at the foot of a mountain across the country, and is also cultivated as a medicinal herb. It has a height of about 60 cm, its several square stems come from the root, its lanceolate leaf are in opposing pairs, its edges are flat, and its lip-shaped purple flowers bloom by forming racemous inflorescence in the stem apex from around July to August. Its fruits are in calyxes and are round. More than 10 species including *S. indica* and *S. fauriei* of *Scutellaria* grow naturally in Korea, Roots of these grasses are used in Chinese medicine, and these grasses are bred by seeds. The Baikl skullcap is a medicine used frequently for the purpose of lowering a fever or detoxification. When collecting its roots and peeling the root bark, it has a yellow like gold. It treats an increasing fever or a chill is felt frequently in the body, and is mainly used for many symptoms caused by a fever in the lungs, and treats fever-related thirst and jaundice, dysentery, diarrhea, dyspepsia, goldthread, as well as a furuncle or tumor in the body, a further worsening carbuncle, and so on. Unusually, commonly used cold medicines are classified as a medicine that should be prohibited for pregnant women, whereas it is known that in the case of roasted Baikl skullcap, it exhibits a good treatment effect even if the pregnant women suffer pain by fetal movement unrest and so on.

Lance Asiabell (*Codonopsis lanceolata* Benth et Hook) is a perennial vine plant belonging to Campahutaceae, and is known that it has an effect on reinforcement of immunity and an anticancer effect. For example, Korean Patent Publication No. 2013-57317 describes that it contributes to the reinforcement of nutrition and has a tonic effect through regulation of proliferation of lymphocyte cells and NO in a macrophage, and regulation of iNOS gene expression and cytokine expression, Korean Patent Publication No. 2008-12813 describes that ethanol extracts and hot water extracts from Lance Asiabell have inhibitory effects on cancer cell proliferation, Korean Patent Publication No. 2006-88129 describes a tablet type functional milk composition that contains *Acanthopanax senticosus* extracts, Lance Asiabell extracts, *Agaricus bisporus* extracts and *Pleurotus ostreatus* extracts, and improves immunological activity, and Korean Patent Publication No. 2007-10963 describes a composition for reinforcing the soyangin immunity, that contains, as active ingredients, several types of uncooked extracts including Lance Asiabell. Also, Korean Patent No. 10-1141779 reports that the saponin fraction of Lance Asiabell promotes hair growth and hair tonic.

When the natural extracts (for example, *Cimicifuga heracleifolia* extracts, Baikl skullcap extracts or Lance Asiabell extracts) used in the composition of the present invention are obtained by treating the natural products with extractants, various extractants may be used. Preferably, a polar solvent or a non-polar solvent may be used. An appropriate example of the polar solvent includes, (i) water, (ii) an alcohol (preferably, methanol, ethanol, propanol, butanol, n-propanol, iso-propanol, n-butanol, 1-pentanol, 2-butoxyethanol, or ethylene glycol), (iii) acetic acid, (iv) dimethyl-formamide (DMFO), and (v) dimethyl-sulfoxide (DMSO). A appropriate example of the non-polar solvent includes, acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethyl amine, ether, carbon tetrachloride and THF.

More preferably, the extractants used in the present invention include, (a) water, (b) an anhydrous or hydrous lower alcohol having from 1 to 4 carbon atoms (methanol, ethanol, propanol, butanol, and so on), (c) a mixed solvent of the lower alcohol and water, (d) acetone, (e) ethyl acetate, (f) chloroform, (g) butyl acetate, (h) 1,3-butylene glycol, (i) hexane, and (j) diethyl ether. Most preferably, the extracts of the present invention are obtained by treating water with *Cimicifuga heracleifolia*, Baikl skullcap or Lance Asiabell dry matters using a hot-water treatment.

The term "extracts" used herein denotes, as described above, crude extracts commonly used in the relevant art, but broadly, includes fractions obtained by additionally fractionating the extracts as well. That is, *Cimicifuga heracleifolia* extracts, Baikl skullcap extracts or Lance Asiabell extracts include not only that obtained by using the above-described extractants, but also that obtained by additionally applying a refining process hereto. For example, *Cimicifuga heracleifolia* extracts, Baikl skullcap extracts or Lance Asiabell extracts of the present invention include, fractions obtained by allowing the extracts to pass through an ultrafiltration membrane having a constant molecular weight cut-off value, and fractions obtained by additionally carrying out the various refining methods such as separation using the various chromatography methods (that have been prepared for separation depending on size, electric charge, hydrophobicity or hydrophilicity) as well.

*Cimicifuga heracleifolia* extracts, Baikl skullcap extracts or Lance Asiabell extracts used in the present invention may be produced in a powder state by an additional process such as distillation under reduced pressure and freeze-drying or spray-drying.

According to a preferred embodiment of the present invention, *Cimicifuga heracleifolia* extracts, Baikl skullcap extracts or Lance Asiabell extracts added to the composition of the present invention are used in a range of 0.5 to 100 mg/ml, more preferably 0.5 to 50 mg/ml, even more preferably 1 to 25 mg/ml, and most preferably 1 to 10 mg/ml.

Human hair is on the order of 100,000 to 150,000, and each hair grows and is eliminated by going through anagen, catagen and telogen in a different cycle. This cycle is repeated over 3 to 6 years, and as a result, an average of 50 to 100 hairs per day is normally eliminated. A mechanism of hair loss has yet not been identified accurately. However, generally, it is known to be caused by an unbalanced diet, excessive drinking and smoking, drug use, a lack of sleep, excessive stress, childbirth, a menopausal disorder, frequent perms and dyeing, a hormone imbalance, and so on. The hair growing in a human head maintains a constant density as the action by which the hair is born, grows, and falls out is repeated. However, when hair loss progresses by the above-described various causes, first, the hair on top of the head or forehead starts to become thin or weak while the amount of hair loss increases. That is, hair puts its roots in the scalp and receives nutrients from the blood. When hair reaches a state in which the capillaries reduce and the scalp becomes thin over a long period of time, and thus the hair cannot develop normally, the hair in the part is getting thinner and thus lifespan of the hair in the particular part is shortened. The hair of which the lifespan is shortened, may fall out readily, as well as, hair may not be regenerated again in the hair follicles in which the hair has fallen out, ultimately, a symptom of the lack of hair appears.

According to a preferred embodiment of the present invention, hair loss treatment or improvement by the photosensitizer-peptide conjugate of the present invention promotes hair growth or hair generation.

As demonstrated in the examples below, the photosensitizer-peptide conjugate of the present invention performs a function to promote the hair growth through the animal experiments very highly. Accordingly, the composition of the present invention is effective in improving or increasing the hair growth According to a preferred embodiment of the present invention, the composition of the present invention is a pharmaceutical composition which contains (a) a pharmaceutically effective amount of the above-described photosensitizer-peptide conjugate of the present invention; and (b) a pharmaceutically acceptable carrier.

The term "a pharmaceutically effective amount" used herein denotes an amount sufficient to achieve the efficacy or activity of the above-described photosensitizer-peptide conjugate.

The pharmaceutically acceptable carrier contained in the pharmaceutical composition of the present invention is used usually in the formulation. For example, it includes lactose, dextrose, sucrose, sorbitol, mannitol, starches, gum acacia, calcium phosphate, alginate, gelatin, calcium silicate, microcrystalline cellulose, polyvinyl pyrrolidone, cellulose, water, syrup, methyl cellulose, methyl hydroxy benzoate, propyl hydroxyl benzoate, talc, magnesium stearate, mineral oil, and so on, but is not limited to these. The pharmaceutical composition of the present invention further includes, in addition to the above ingredients, lubricants, wetting agents, sweeteners, flavoring agents, emulsifying agents, suspending agents, preservatives, etc. An appropriate example of the pharmaceutically acceptable carrier and formulation is described in Remington's Pharmaceutical Sciences ($19^{th}$ ed., 1995).

The pharmaceutical composition of the present invention may be produced, in unit dosage form, by using the pharmaceutically acceptable carrier and/or a excipient to formulate, or may be produced by placing it in a large-capacity container, according to a method that one of ordinary skill in the art to which this invention belongs may easily embody. At this time, the dosage form may be a form of a solution in oil or an aqueous medium, a suspension or an emulsion, or may be a form of extracts, powders, granules, a tablet, a capsule, or a gel (e.g., hydrogel), and may further include a dispersant or a stabilizer.

Also, the composition of the present invention may be administered in any method, its parenteral administration or oral administration is possible, and it is produced in an appropriate dosage form according to the method of administration. The composition in accordance with the present invention may be produced by an ordinary method according to the dosage form. The dosage form is not particularly limited as long as it can exhibit the effect of the present invention. For example, the dosage form may have a solubilizing agent such as a tonic, an emulsifier such as latex and a cream, or any dosage form such as an ointment, dispersed liquid, a gel, an aerosol, and a mousse. Moreover, a form of the product is also a form of drugs, quasi-drugs, or cosmetics for hair care for the purposes of a hair tonic effect such as hair loss prevention, hair growth, hair restoration, and so on. For example, a form of the product may have any form such as hair growth promoters, hair nourishments, scalp treatments, soaps, hair tonic, shampoos, rinses, hair packs, lotions, conditioners, hair oils, mousses, and creams. Also, the composition of the present invention may be used in a form such as a solid formulation, a solution, an emulsion, a dispersant, a micelle, a liposome, and an ointment, and an organic or an inorganic carrier or an excipient suitable for an oral or a parenteral application may be included also. The composition of the present invention may be mixed with a generally non-toxic, pharmaceutically acceptable carrier, for example, for tablets, powders, pellets, capsules, suppositories, solutions, emulsions, suspensions, liquid formulations, jellies and any other form suitable for use. An example of a usable carrier includes a solid phase, a semisolid phase or a liquid phase of glucose, lactose, gum arabic, gelatin, mannitol, starch paste, magnesium trisilicate, talc, corn starch, keratin, colloidal silica, potato starch, urea, a triglyceride having an intermediate chain length, dextran, and other carriers suitable for use in the production of the formulation. Also, an adjuvant, a stabilizer, a thickener, a coloring agent and a flavoring agent may be used.

Another aspect of the present invention provides a method for screening for a hair growth promoter using light irradiation, including the following steps of:

(a) treating a part from which hair has been removed in an animal skin with a peptide coupled to a photosensitizer (photosensitizer-peptide conjugate);

(b) performing light irradiation on the part from which hair has been removed; and (c) observing the degree of hair growth improvement or promotion in the part from which hair has been removed with the naked eye, wherein when the photosensitizer-peptide conjugate causes hair growth improvement or promotion in the part from which hair has been removed, the photosensitizer-peptide conjugate is determined as a hair growth promoter.

Since the method of the present invention contains as an active ingredient the above-described photosensitizer-peptide conjugate of the present invention, common information between the two will be omitted in order to avoid undue complexity of this specification.

According to the method of the present invention, first, the photosensitizer-peptide conjugate (preferably, ALA-GHK) of the present invention is added to the part from which hair has been removed in an animal. The part from which hair has been removed, is not particularly limited, preferably the animal's back part.

Subsequently, light is applied to the part from which hair has been removed.

According to a preferred embodiment of the present invention, LED radiation is used for the activation of the photosensitizer which is contained as an active ingredient in the composition of the present invention. According to a preferred embodiment of the present invention, it is effective that a wavelength of the LED radiation for the composition of the present invention is a long wavelength, more preferably from 650 to 675 nm, most preferably 660 nm.

According to a more preferred embodiment of the present invention, an irradiation time of the LED radiation is from 5 to 20 minutes, more preferably from 5 to 15 minutes, most preferably from 5 to 7 minutes. According to a more preferred embodiment of the present invention, an irradiation distance of the LED is within 10 cm, more preferably within 5 cm, most preferably within 2 cm.

Finally, the degree of hair growth improvement or promotion in the part from which hair has been removed is observed with the naked eye. As a result, if the photosensitizer-peptide conjugate causes hair growth improvement or promotion in the part from which hair has been removed, the photosensitizer-peptide conjugate is determined as a hair growth promoter.

The term "photosensitizer-peptide conjugate" used when referring to the screening method of the present invention denotes an unknown material that is used in screening to examine whether or not the improvement or promotion of hair growth is caused by light irradiation, and may be variously produced depending on the peptide coupled to a photosensitizer.

Still another aspect of the present invention provides a method for improving or promoting hair growth, the method comprising: administering a composition which contains a pharmaceutically effective amount of a peptide coupled to a photosensitizer (photosensitizer-peptide) to a subject.

Advantageous Effects

The features and advantages of the present invention are summarized as follows:

(a) The present invention relates to a composition for improving or promoting hair growth, which contains, as an active ingredient, a photosensitizer-peptide conjugate, and to a method for screening for a hair growth promoter using the active ingredient.

(b) ALA, which is the photosensitizer of the present invention, is preferably activated by LED radiation, and more preferably activated by radiation having a long wavelength of 650 to 675 nm.

(c) The peptide of the present invention is a peptide in which 3 to 7 amino acid residues are incorporated (most preferably, glycine-histidine-lysine), and may cooperate with the photosensitizer to enable very superior hair growth improving or promoting effects using light radiation.

(d) Further, the composition of the present invention may exhibit further superior effects when natural extracts (for example, *Cimicifuga heracleifolia* extracts, Baikl skullcap extracts or Lance Asiabell extracts) are added.

(e) Thus, the composition of the present invention can be significantly advantageously applied to drugs, quasi-drugs, and cosmetics.

DESCRIPTION OF DRAWINGS

FIGS. 21 to 24 illustrate photographic results showing the hair growth promoting effects observed on day 11, day 13, day 15, and day 17 after sample treatment, respectively.

MODES OF THE INVENTION

Figure 1:
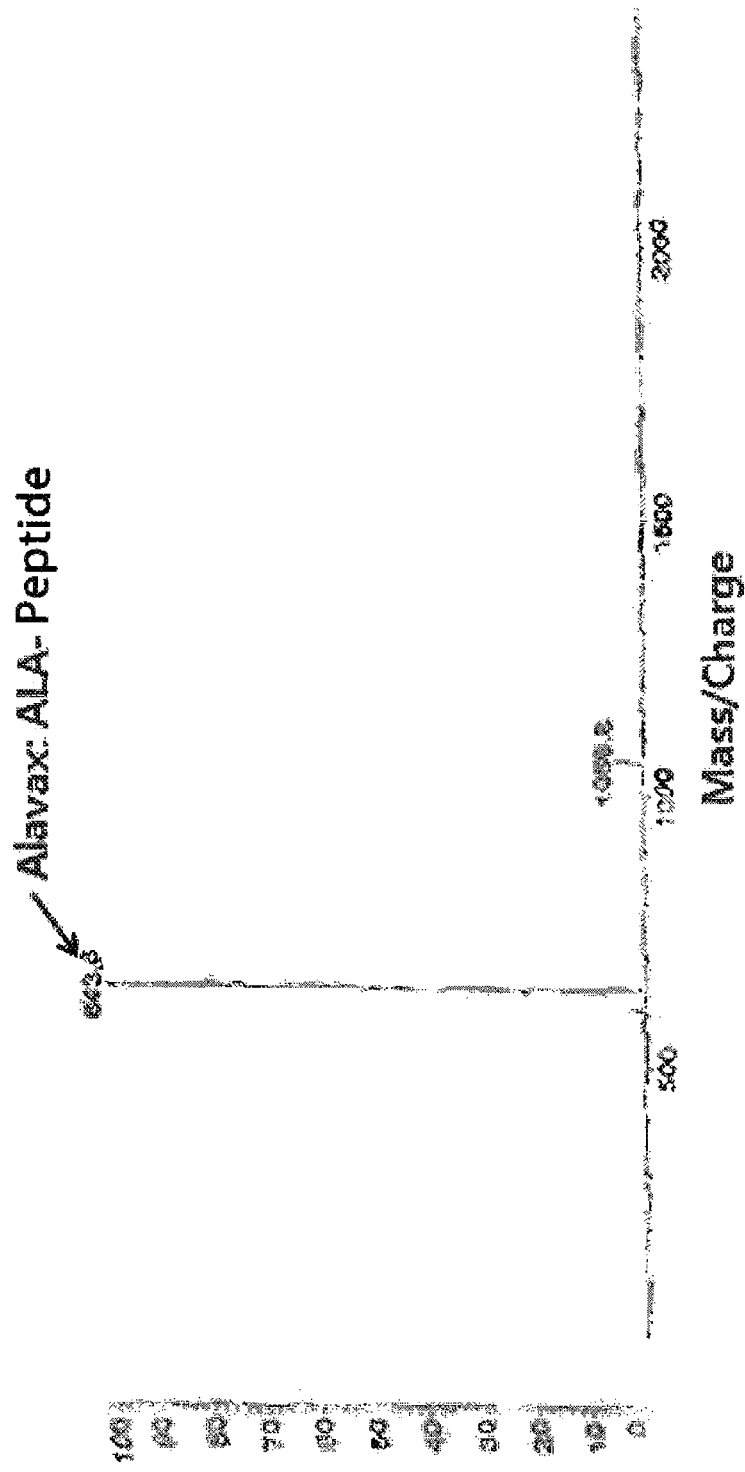
FIG. 1 illustrates a graph showing MALDI-TOF analysis results of ALA-peptide (GHK).

Hereinafter, the present invention will be described through examples in further detail. It will be apparent to one of ordinary skill in the art that these examples are only for the purpose of describing the present invention more particularly and the scope of the present invention in accordance with the subject matter of the present invention is not limited to these examples.

Examples

Experimental Materials and Experimental Method

Production of Natural Extracts Through Hot Water Extraction

A 10-fold volume of primary distilled water was put into 100 g of *Cimicifuga heracleifolia*, Baikl skullcap, and Lance Asiabell dry matters, which were hot water extracted for 6 hours at 100° C. and were then filtered. The filtered extracts were pulverized through freeze-dried and then stored at 4° C. until used. The pulverized natural extracts were used in a mouse experiment at a concentration of 1 mg/ml.

Production of 5-Aminolevulinic Acid (ALA)-Peptide (GHK)

14.286 g (substitution rate, 1.40 mmole/g; 20 mmole) of 2-chlorotrityl resin (MERCK, USA), 18.742 g of Fmoc-Lys (Boc)-OH (40 mmole; MERCK, USA), and 13.97 ml of N,N-diisopropylethylamine (DIEA) (80 mmole; MERCK, USA) were mixed in a glass reactor for peptide synthesis (Daekwang Science, KOR) to which a filter (0.1 μm; Sigma, USA) was attached. After that, 400 ml of methylene chloride (MC; Merck, USA) was added thereto, which was reacted for 5 or more hours. 10 ml of methanol was added to the reaction solution to be reacted for 10 minutes, and then all the solution was removed. The resin was cleaned sequentially with MC, N,N'-dimethylformamide (DMF; Merck, USA) and methanol, and then 400 ml of 20% piperidine (Merck, USA) was added thereto to be reacted 2 times for 20 minutes to remove a Fmoc group. After removing the Fmoc group, the trityl resin was cleaned sequentially with MC and DMF again to remove all of the solution. While the Fmoc group was removed, 24.789 g of Fmoc-His(Trt)-OH (40 mmole; MERCK, USA), 5.40 g (40 mmole) of 1-hydroxybenzotriazole (HOBt; MERCK, USA), and 6.19 ml (40 mmole) of diisopropylcarbodiimide (DIC; MERCK, USA) were completely dissolved in 100 ml of DMF to be activated for 40 minutes. The activated Fmoc-His(Trt)-OH/DMF solution was added to the resin from which Fmoc was removed, and 300 ml of DMF was also added thereto to be reacted for 5 or more hours. After reacting for 5 or more hours, the solution was completely removed, the resin was cleaned sequentially with MC and DMF, and then 400 ml of 20% piperidine was added thereto to be reacted 2 times for 20 minutes to remove a Fmoc group. After removing the Fmoc group, the trityl resin was cleaned sequentially with MC and DMF again to remove all of the solution. While the Fmoc group was removed, 11.892 g of Fmoc-Gly-OH (40 mmole; MERCK, USA), 5.40 g (40 mmole) of HOBt, and 6.19 ml (40 mmole) of DIC were completely dissolved in 100 ml of DMF to be activated for 40 minutes. The activated Fmoc-Gly-OH/DMF solution was added to the resin from which Fmoc was removed, and 300 ml of DMF was also added thereto to be reacted for 5 or more hours. After reacting for 5 or more hours, the solution was completely removed, the resin was cleaned sequentially with MC and DMF, and then 400 ml of 20% piperidine was added thereto to be reacted 2 times for 20 minutes to remove a Fmoc group. After removing the Fmoc group, the trityl resin was cleaned with MC and DMF again to remove all the solution. While the Fmoc group was removed, 5.245 g of ALA (40 mmole; Sigma, St. Louis, Mo., USA) was completely dissolved in 100 ml of DMF to be activated for 40 minutes. The activated Ala/DMF solution was added to the resin from which Fmoc was removed, and then 300 ml of DMF was also added thereto to be reacted for 5 or more hours. After reacting for 5 or more hours, the solution was completely removed, the resin was cleaned with MC, DMF and MC, and then the solution was completely removed. 600 to 800 ml of 95% trifluoroacetic acid (TFA) aqueous solution (MERCK, USA) was added to the resin from which solution was removed, which was reacted for 3 hours, and then the resulting solution was collected in a separate container. The collected solution was added slowly to cold (4° C.) ether (SIGMA, USA) to induce precipitation, which was left to stand in a freezer for 20 minutes so that the peptide in the solution was completely precipitated. The precipitated peptide was recovered by centrifugation and the remaining ether was completely vaporized, which was then analyzed and refined by high performance liquid chromatography (HPLC; WATERS, USA).

Structure Analysis of ALA-Peptide

A MALDI-TOF (matrix-assisted laser desorption ionization) instrument was used, along with an Axima CFR, a Kratos instrument, in which a gauge pressure was set to $8.0 \times 10^{-4}$ pascals, and the samples along with a matrix were put into a 96 square-well sample plate with linear modes to be analyzed. The matrix used together with the analysis has used cinnamic acid (a-cyano-4-hydroxycinnamic acid (CHCA); CAS Number, 28166-41-8) (see FIG. 1).

Concentration of ALA and ALA-Peptide

ALA and ALA-peptide which were major test materials of the present invention were dissolved in pure water to a concentration of 100 mg/ml (100 ppm) to be used.

Hair Growth Promoting Effects Using a Mouse

A 7-week-old C57BL/6N mouse (Jungang Lab. Animal Inc., KOR) was used for this study, and hair of the mouse's back was completely removed using a wax at the age of 49 days to 51 days at which the C57BL/6N mouse enters catagen for the second time. In order to verify hair growth promoting effects of the test materials, it was treated once a day for 24 days. More particularly, ALA and the ALA-peptide were sprayed 3 times before LED radiation, and the LED treated groups were verified after being treated for 5 minutes. Compositions of the test materials for this test are shown in Table 1 below.

TABLE 1

Treatment compositions of test materials of first test group

| No. | Treatment material |
|---|---|
| 1 | Untreated (control group) |
| 2 | LED-Red |
| 3 | LED-Red + Ala1 (ALA) |
| 4 | LED-Red + Ala2 (ALA-peptide) |
| 5 | LED-Blue |
| 6 | LED-Blue + Ala1 (ALA) |
| 7 | LED-Blue + Ala2 (ALA-Peptide) |

Experimental Results

Measurements of Hair Growth Promoting Effects Using a Mouse (First Test)

Figure 2:
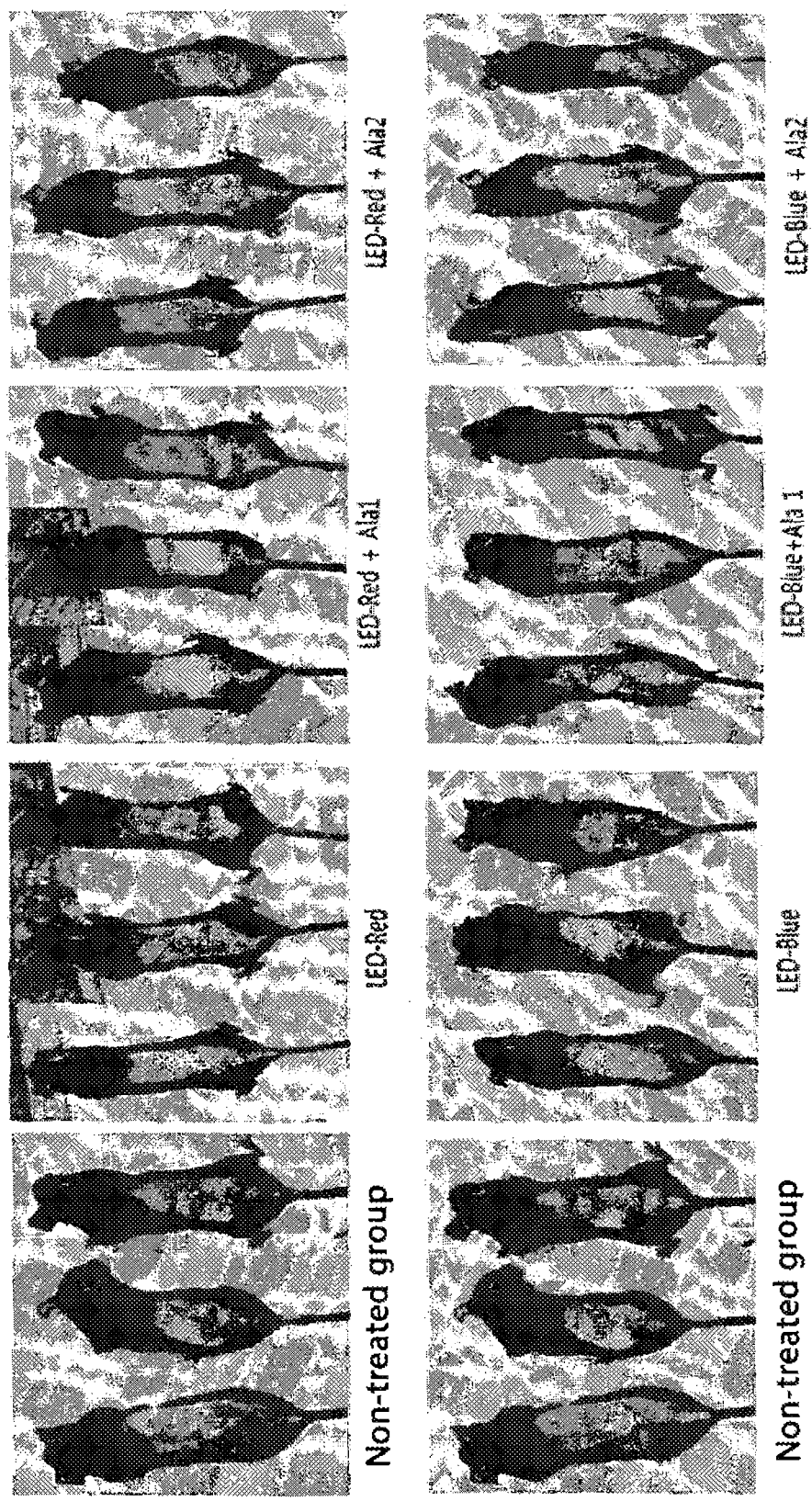
FIG. 2 illustrates photographic results on day 0 after sample treatment after removing hair in a mouse's back.
Figure 3:
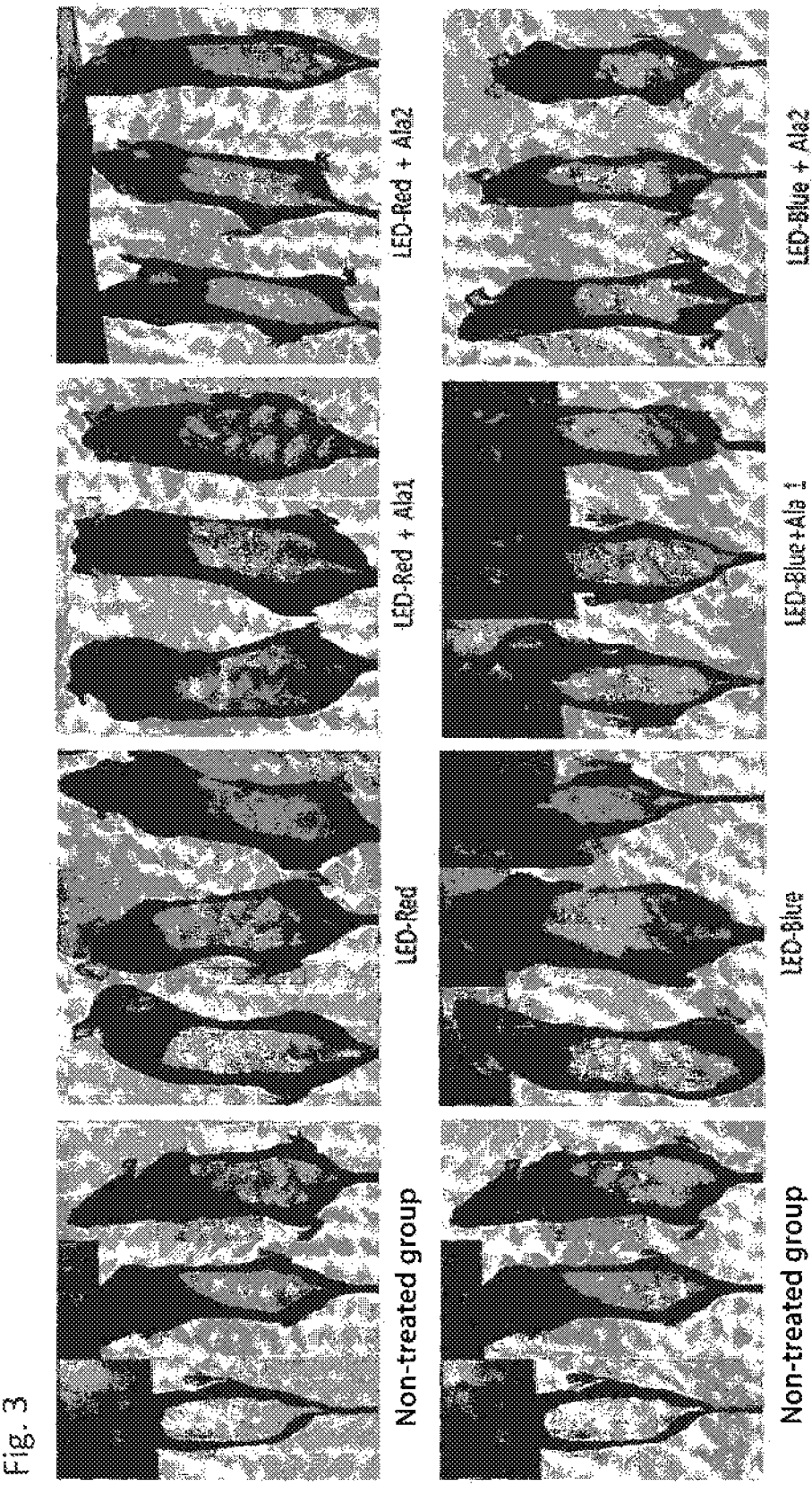
FIGS. 3 to 5 illustrate photographic results showing the hair growth promoting effects observed on day 3, day 5, and day 8 after sample treatment, respectively.
Figure 4:
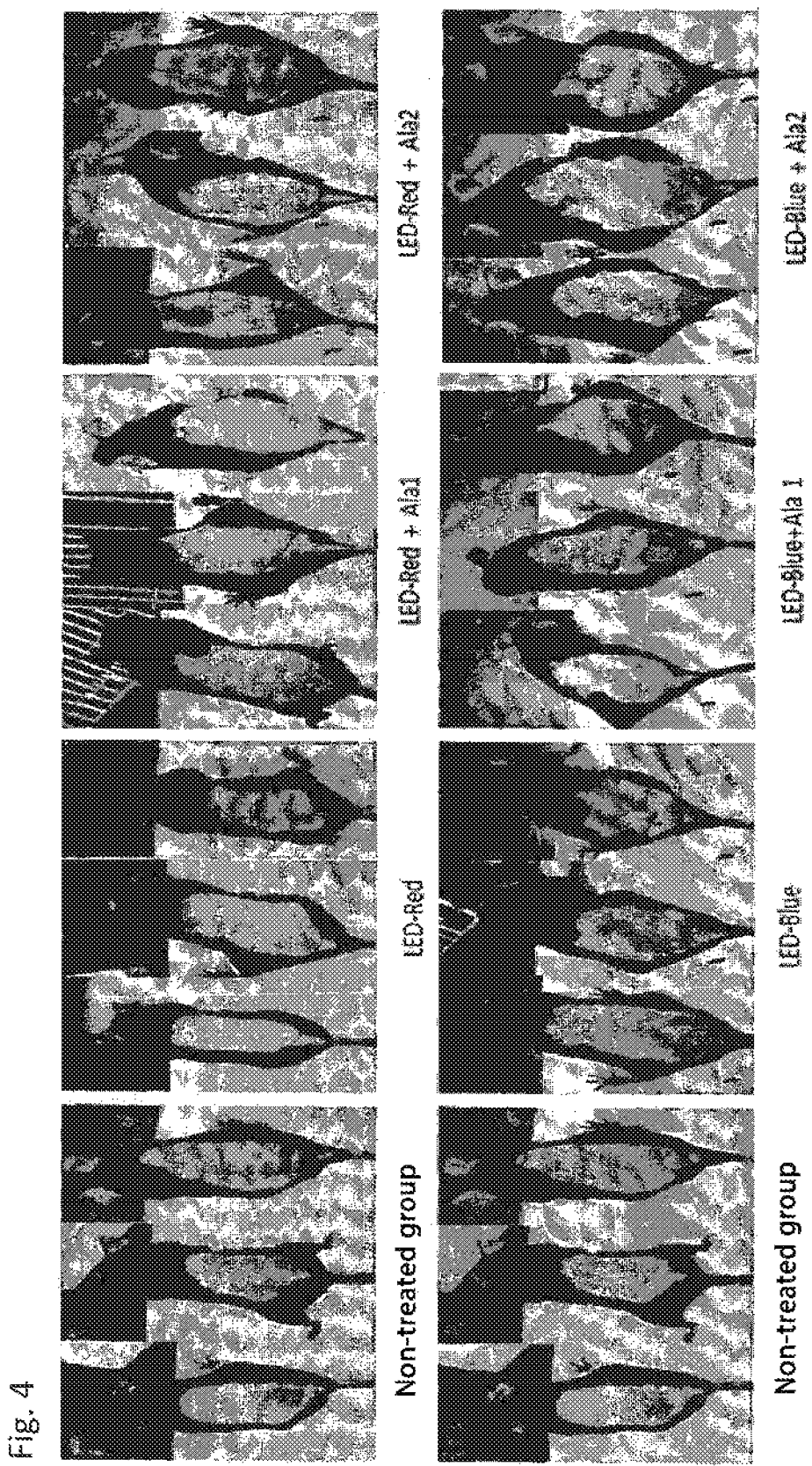
Figure 5:
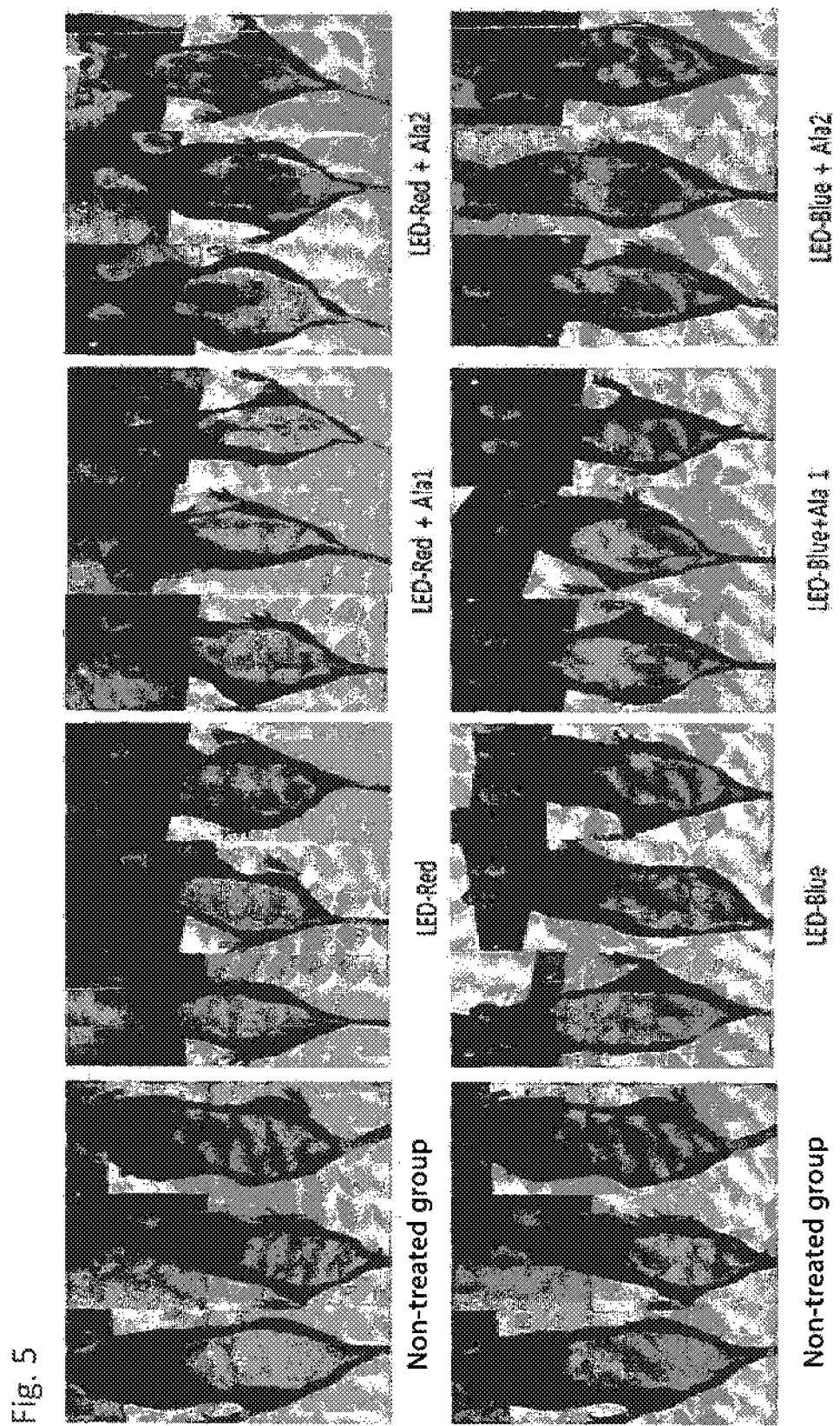
Figure 6A:
FIG. 6A illustrates photographs showing the hair growth promoting effects of the treated samples compared to an untreated group.
Figure 6B:
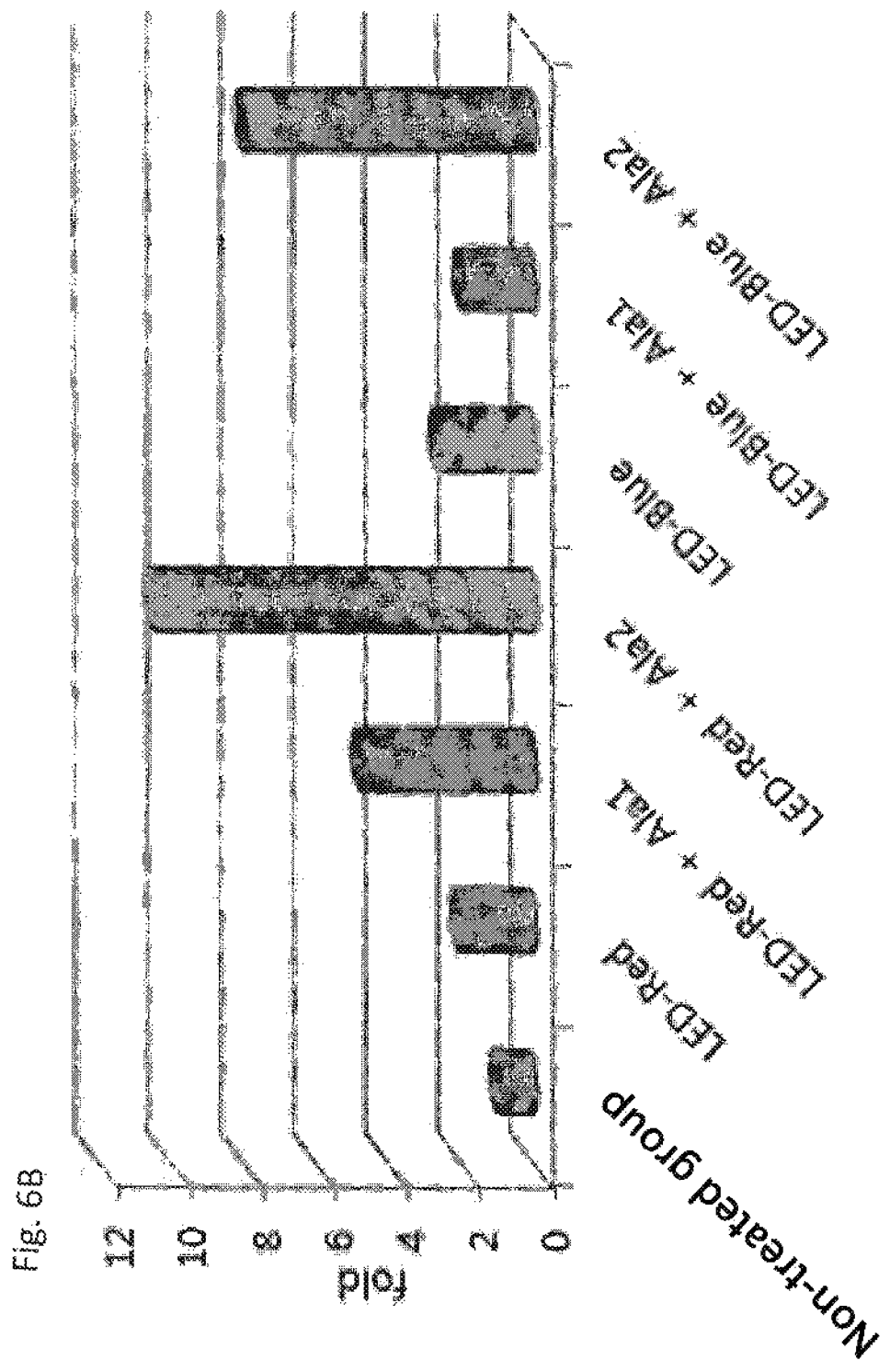
FIG. 6B illustrates a graph showing a result quantifying the hair growth promoting effects of the treated samples compared to an untreated group.

As a result of the treatment to the mouse to verify the hair growth effects of the ALA-peptide of the present invention, there were no differences in hair growth levels in an untreated group, an LED-Red radiation group, an LED-Red+ALA treated group, LED-Blue and LED-Blue+ALA treated groups until day 3 (see FIGS. 2 and 3). However, the hair growth promoting effects of the sample began to appear on day 5 after sample treatment. Particularly, an LED-Red+ALA-peptide treated group and an LED-Blue+ALA-Peptide treated group began to show distinct differences with the naked eye compared to the untreated group (see FIG. 4). On day 8 after sample treatment, a clear hair growth promoting effect was observed in the LED-Red+ALA-peptide treated group, and it exhibited about 10-fold hair growth promoting effects compared to the untreated group. Also, the LED-Blue+ALA-peptide treated group exhibited about 7-fold hair growth promoting effects compared to the untreated group (see FIGS. 5, 6A and 6B).

Figure 7:
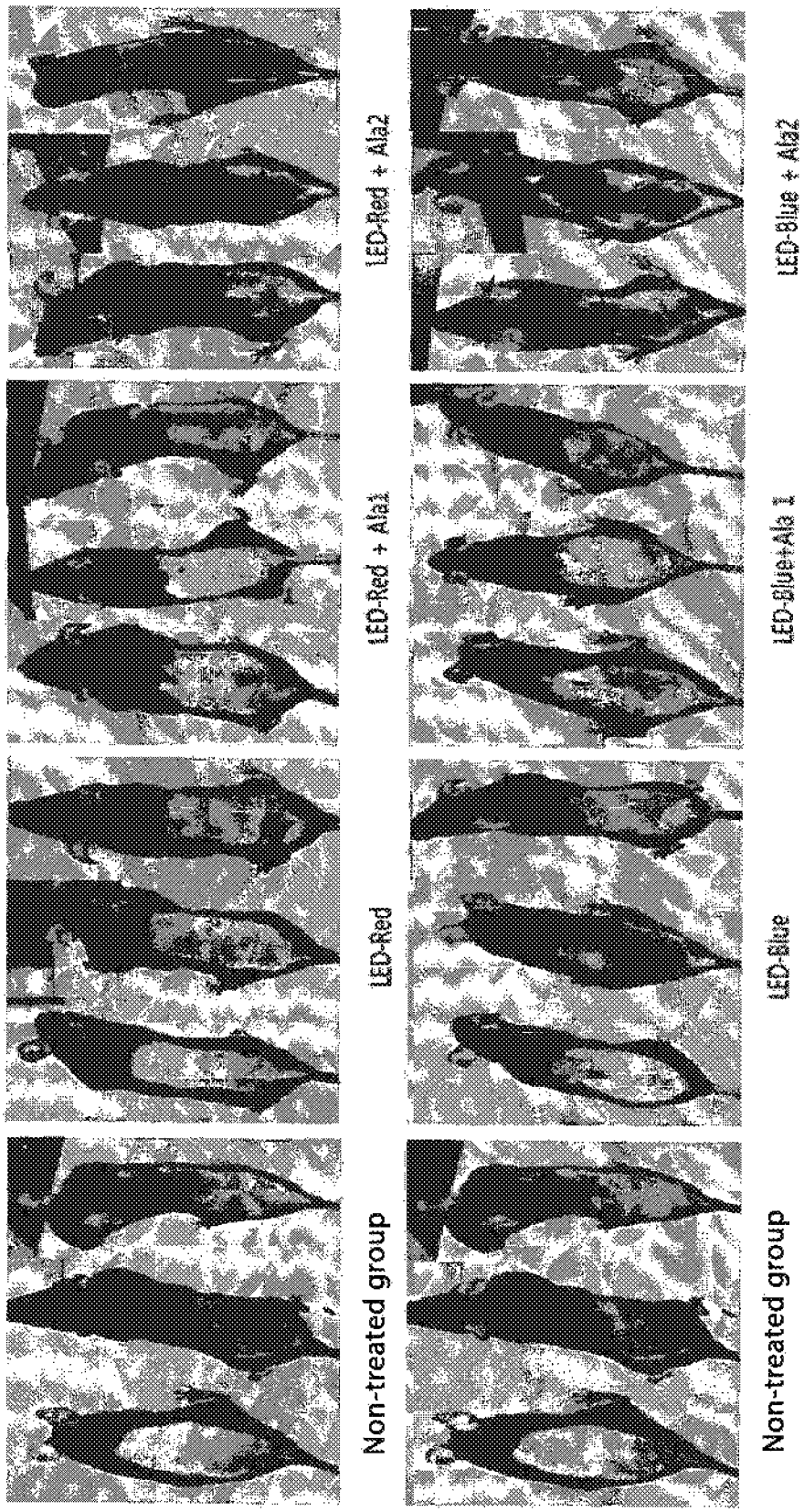
FIGS. 7 to 13 illustrate photographic results showing the hair growth promoting effects observed on day 10, day 12, day 14, day 16, day 19, day 22, and day 24 after sample treatment, respectively.
Figure 8:
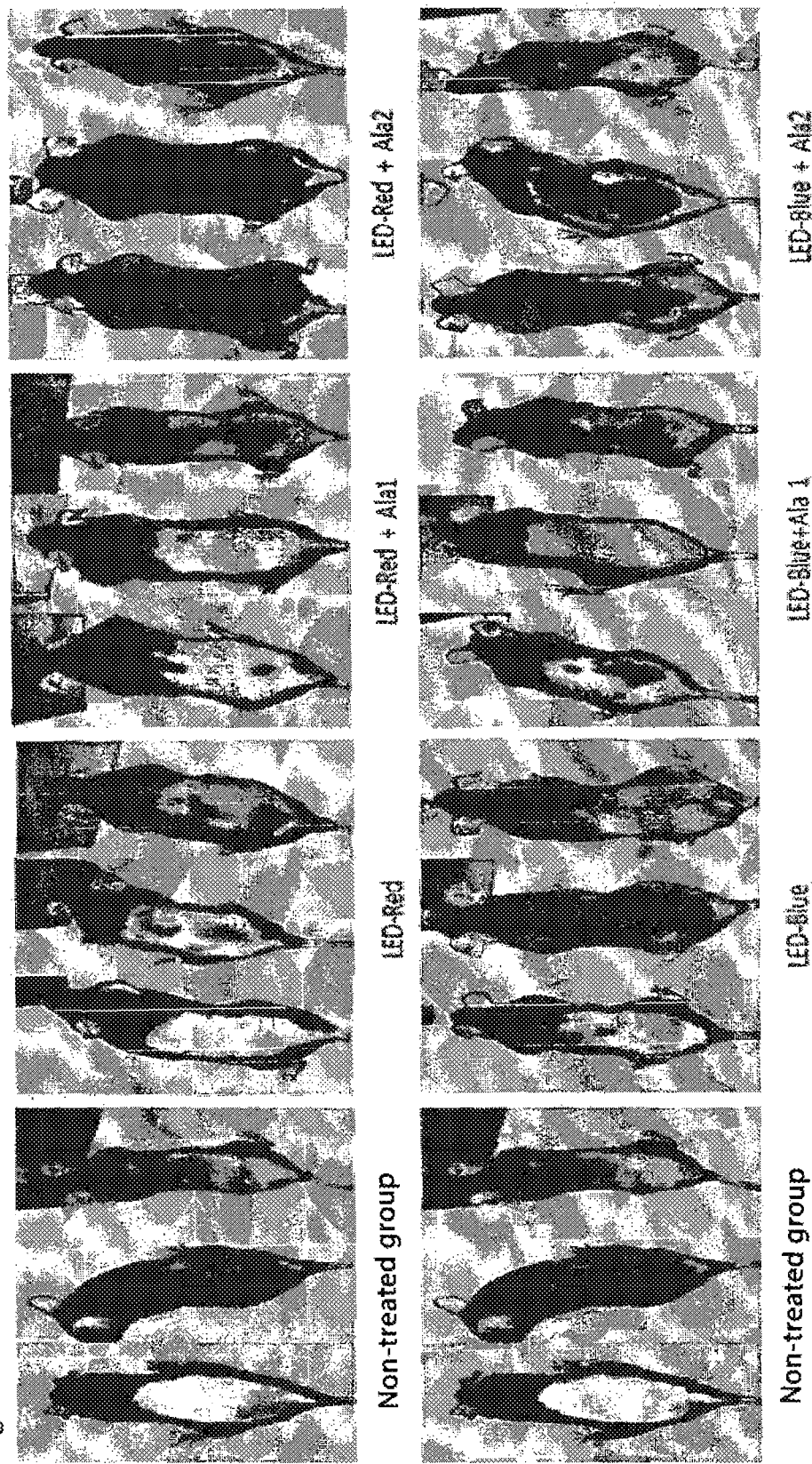
Figure 9:
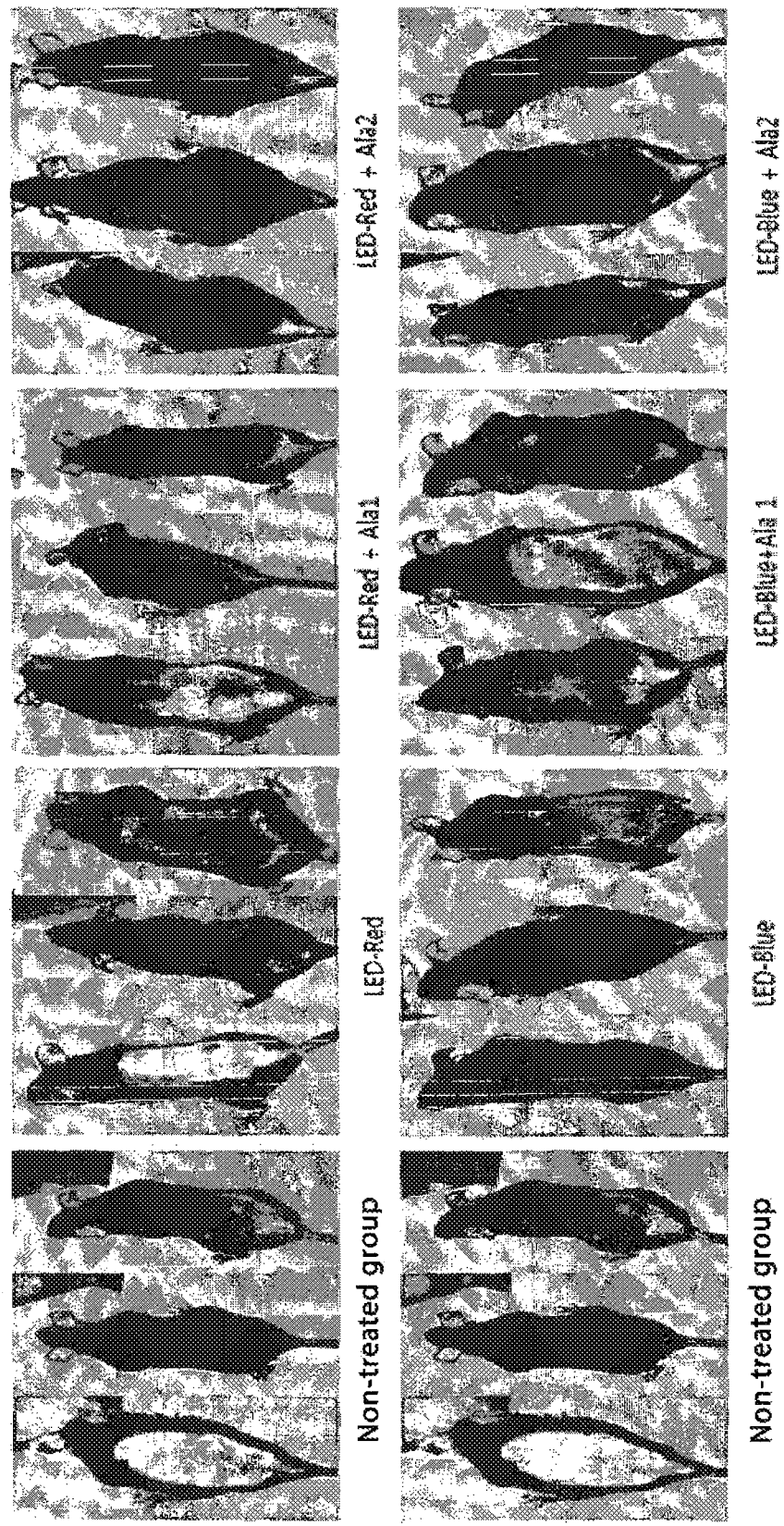
Figure 10:
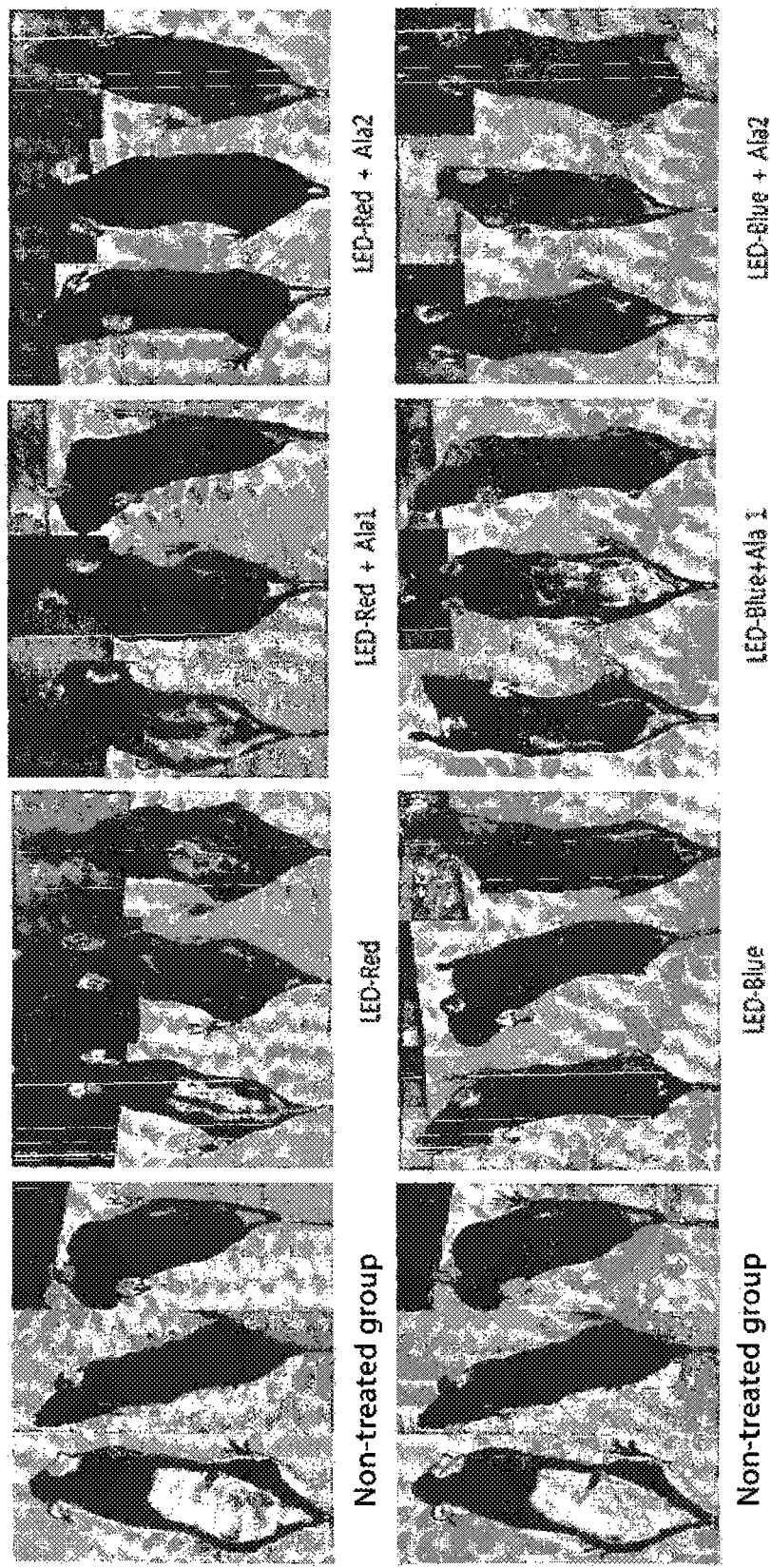
Figure 11:
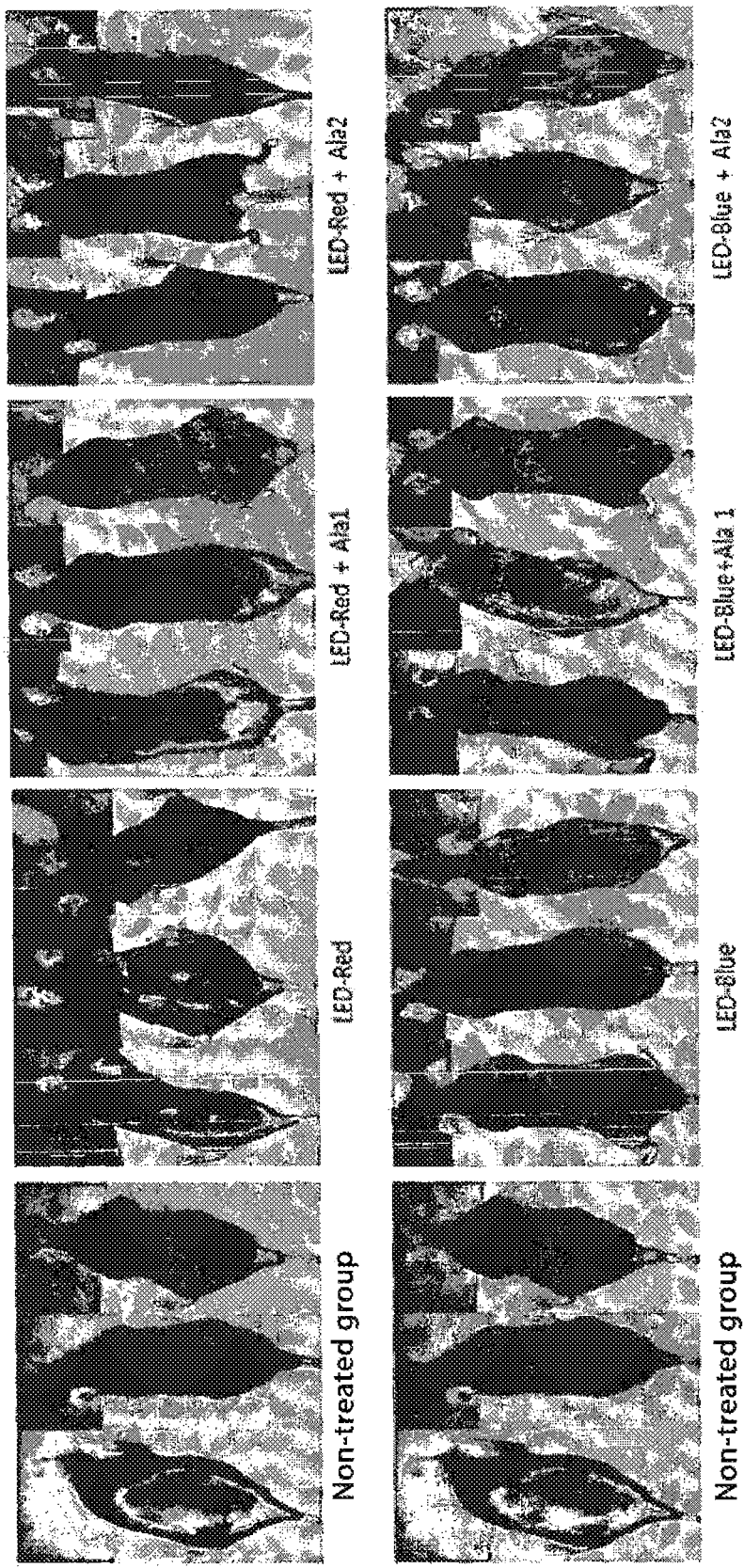
Figure 12:
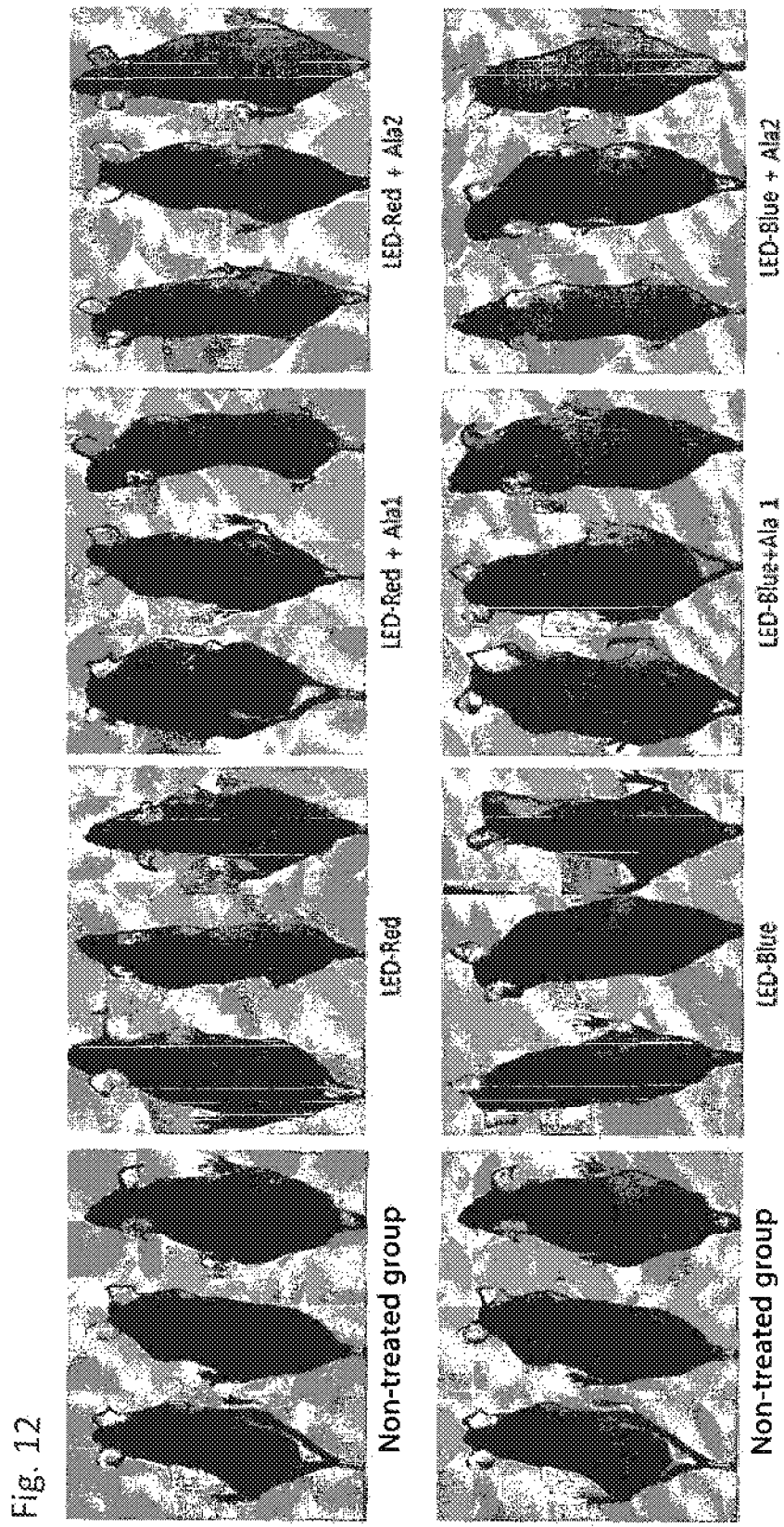
Figure 13:
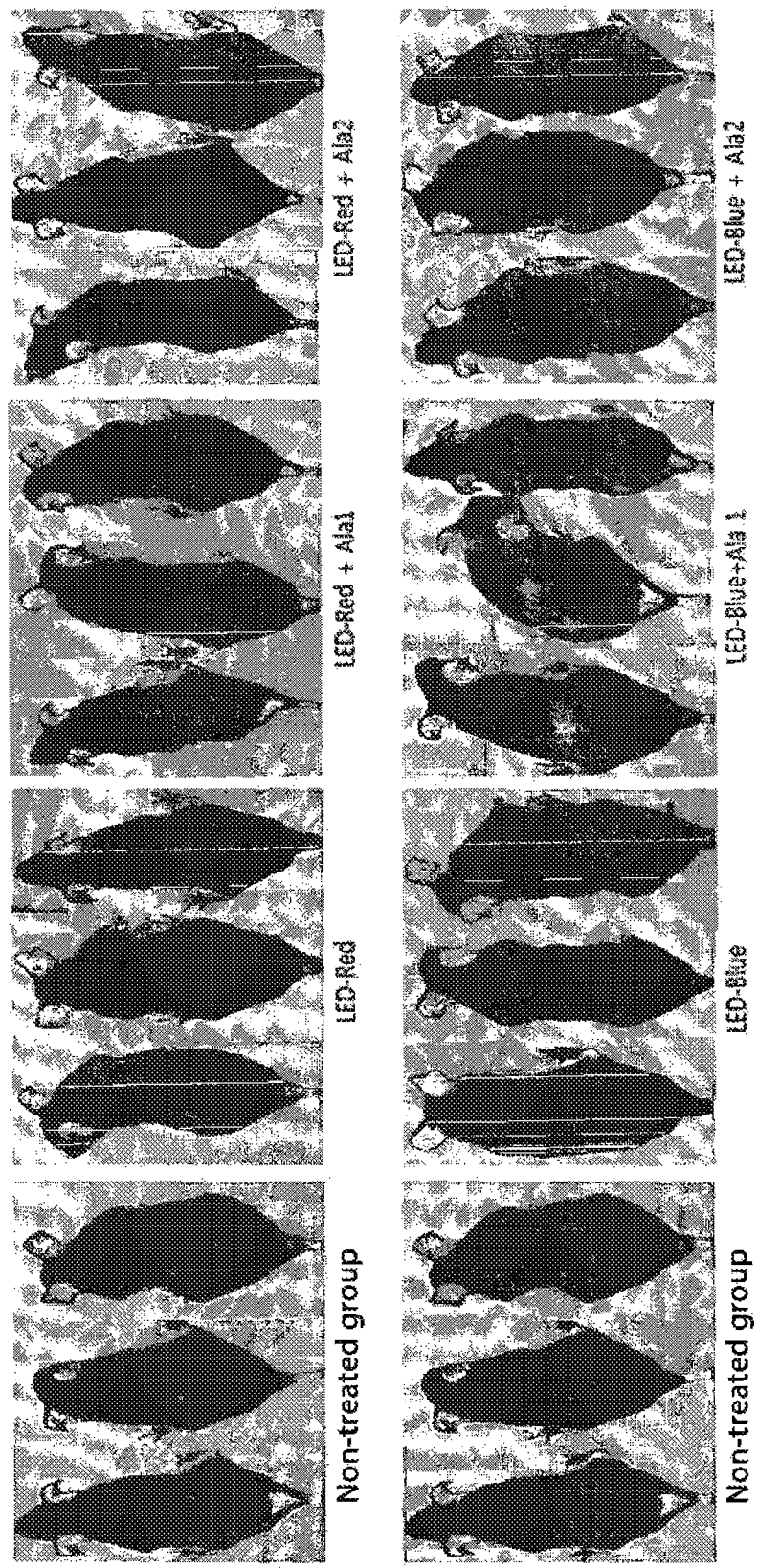
Figure 14:
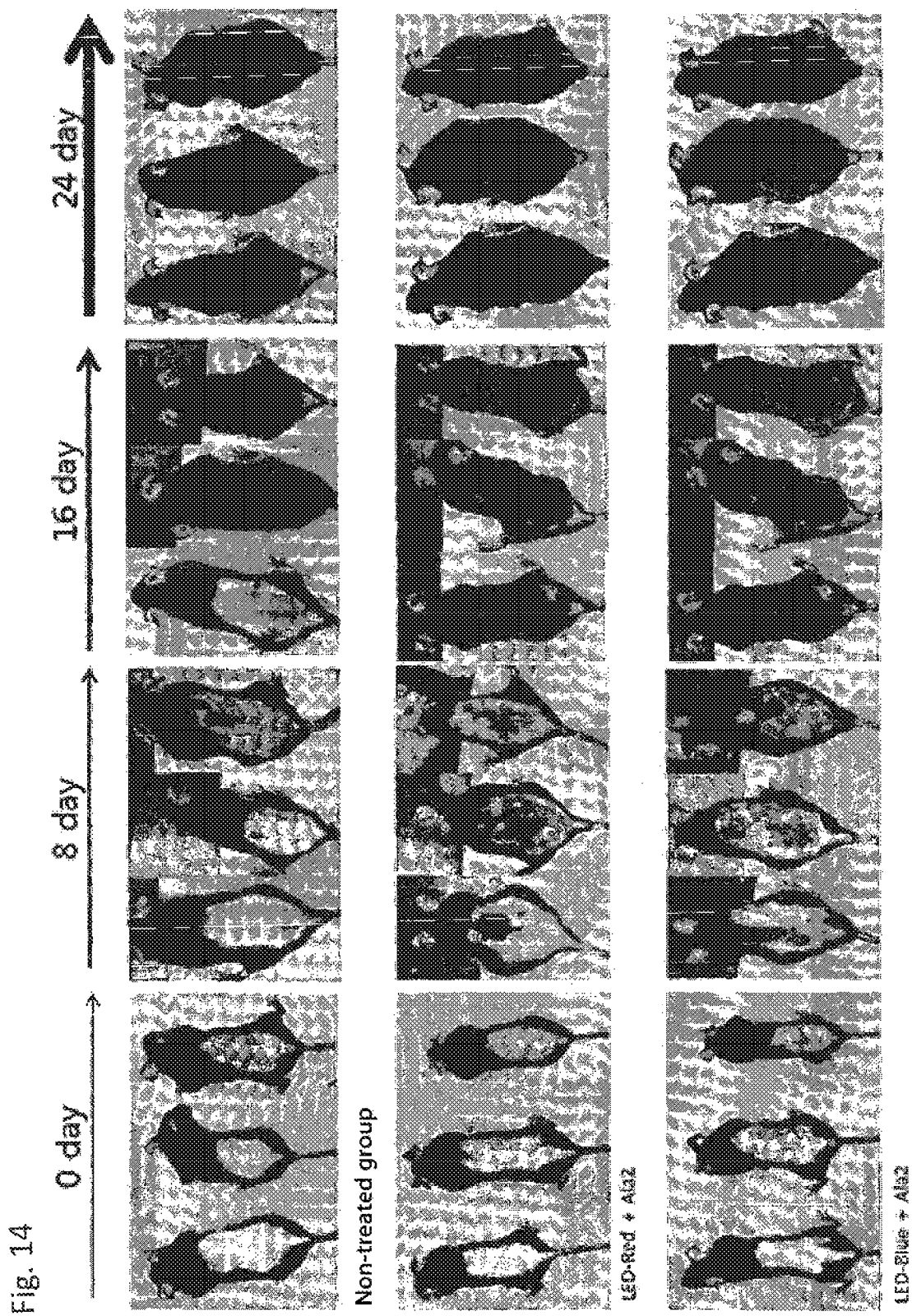
FIG. 14 illustrates photographic results showing the significant hair growth promoting effects of an LED-Red+ALA-peptide (Ala2) treated group and an LED-Blue+ALA-peptide treated group compared to an untreated group.

Surprisingly, in the LED-Red+ALA-peptide and LED-Blue+ALA-peptide treated groups, increasing effects in the hair growth amounts due to significant hair growth promoting effects compared to the control group were observed, and most superior hair growth promoting effect was observed in the LED-Red+ALA-peptide (see FIGS. 7 and 8).

As a result of observation to hair growth promoting effects through continuous treatments of the LED-Red+ALA-peptide and LED-Blue+ALA-peptide, it was confirmed that LED-Red+ALA-peptide treated group exhibited more superior hair growth promoting effects than the LED-Blue+

Figure 15:
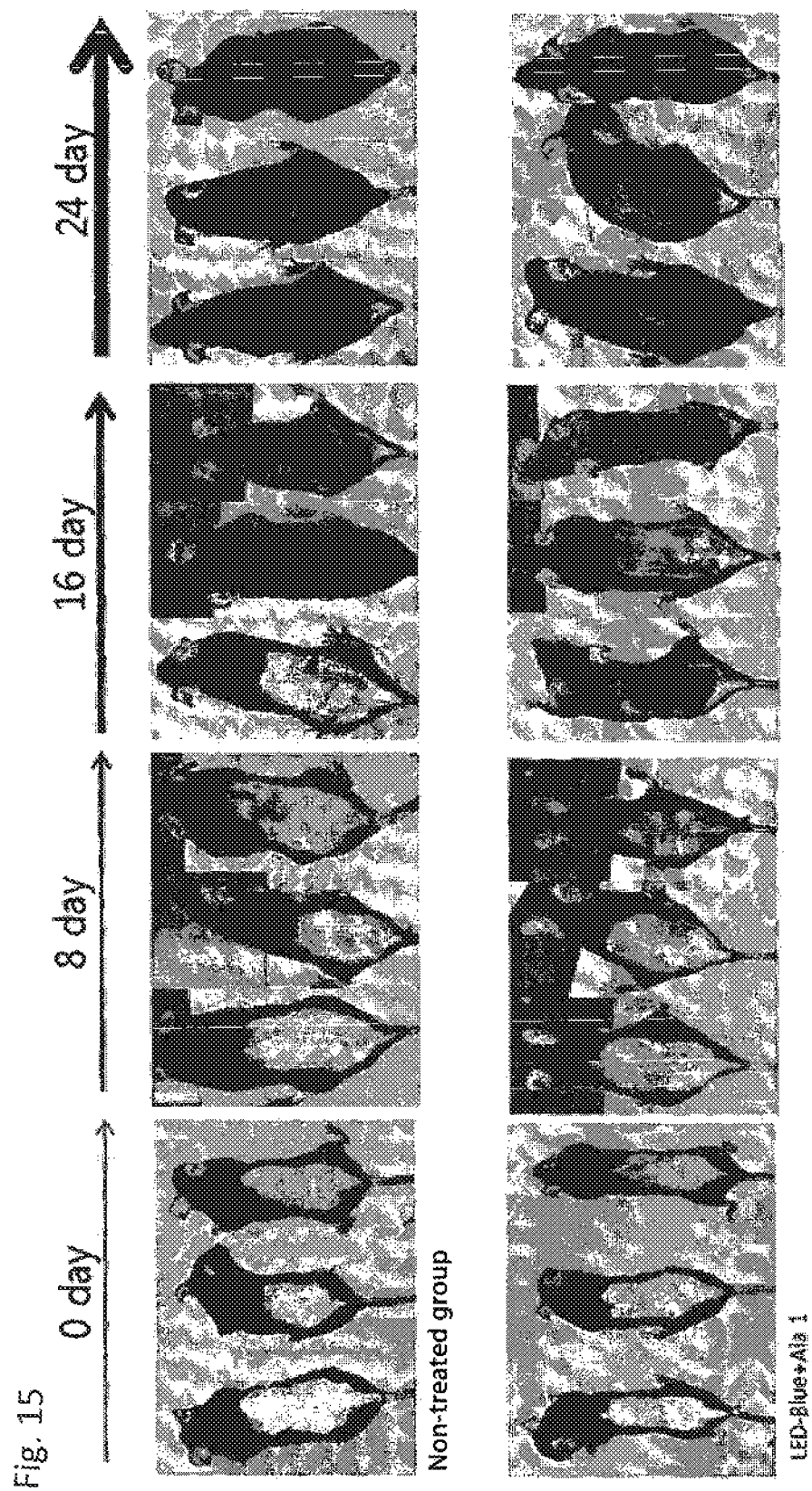
FIG. 15 illustrates photographic results showing the hair loss phenomenon of an LED-Blue+ALA treated group compared to an untreated group.
Figure 16:
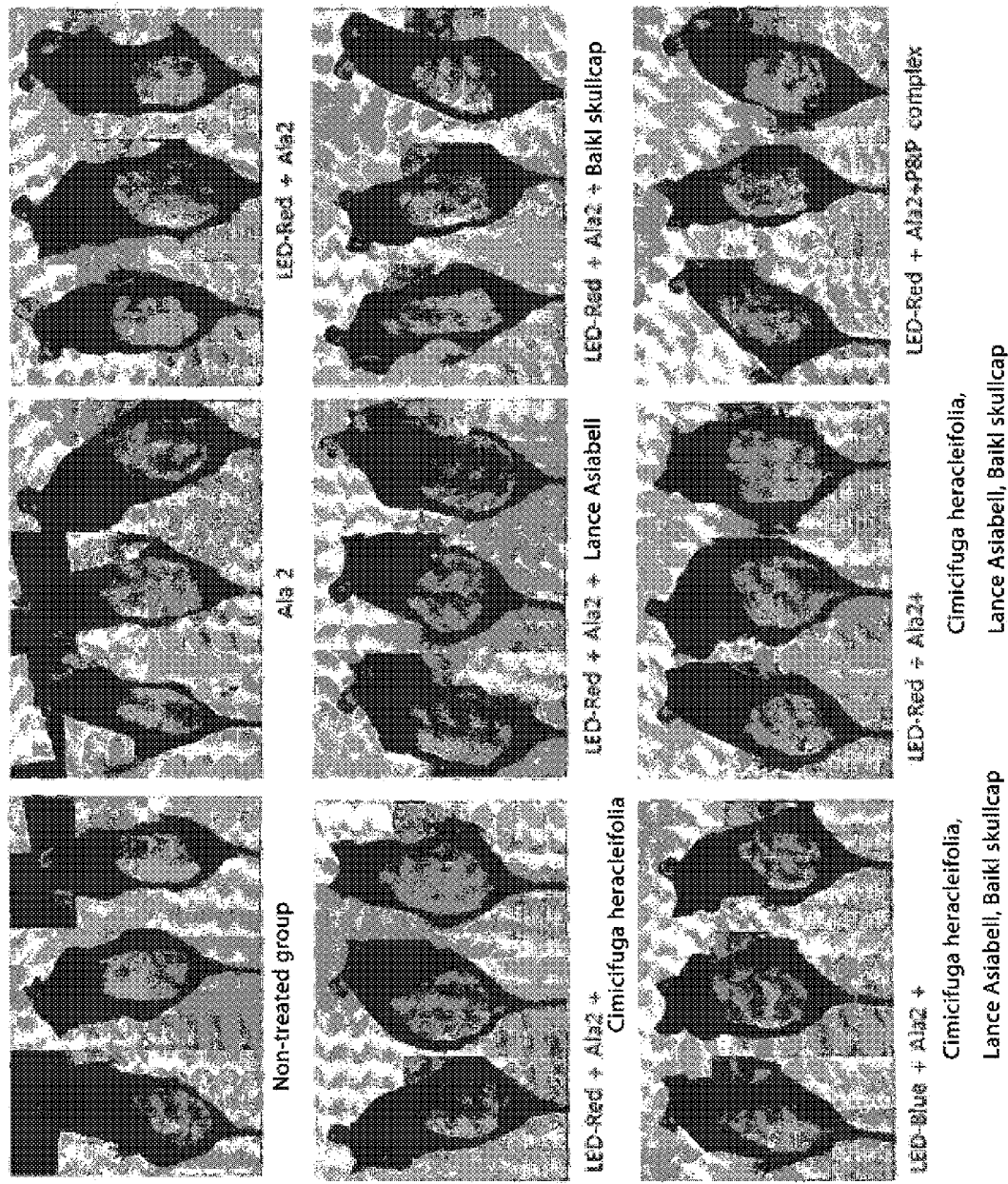
FIG. 16 illustrates photographic results on day 0 after sample treatment after removing hair in a mouse's back. The treated samples are as follows: an untreated group, ALA-peptide (Ala2), LED-Red-Ala2, LED-Red-Ala2+*Cimicifuga heracleifolia* (1 mg/ml), LED-Red-Ala2+Lance Asiabell (1 mg/ml), LED-Red-Ala2+Baikl skullcap (1 mg/ml), LED-Blue-Ala2+Cimicifuga *heracleifolia*+Lance Asiabell+Baikl skullcap, LED-Red-Ala2+*Cimicifuga heracleifolia*+Lance Asiabell+Baikl skullcap, and LED-Red-Ala2+P&P complex. The P&P complex is a complex of a protein and peptide, that is, a complex including proteins composed of IGF (2 ppm), SOD (2 ppm), thymosin-beta-4 (2 ppm) and TGF-beta (2 ppm), and peptides composed of Keratin scalp peptide (20 ppm), Elastin essential & hair peptide (20 ppm) and thymopeptin (20 ppm).
Figure 17:
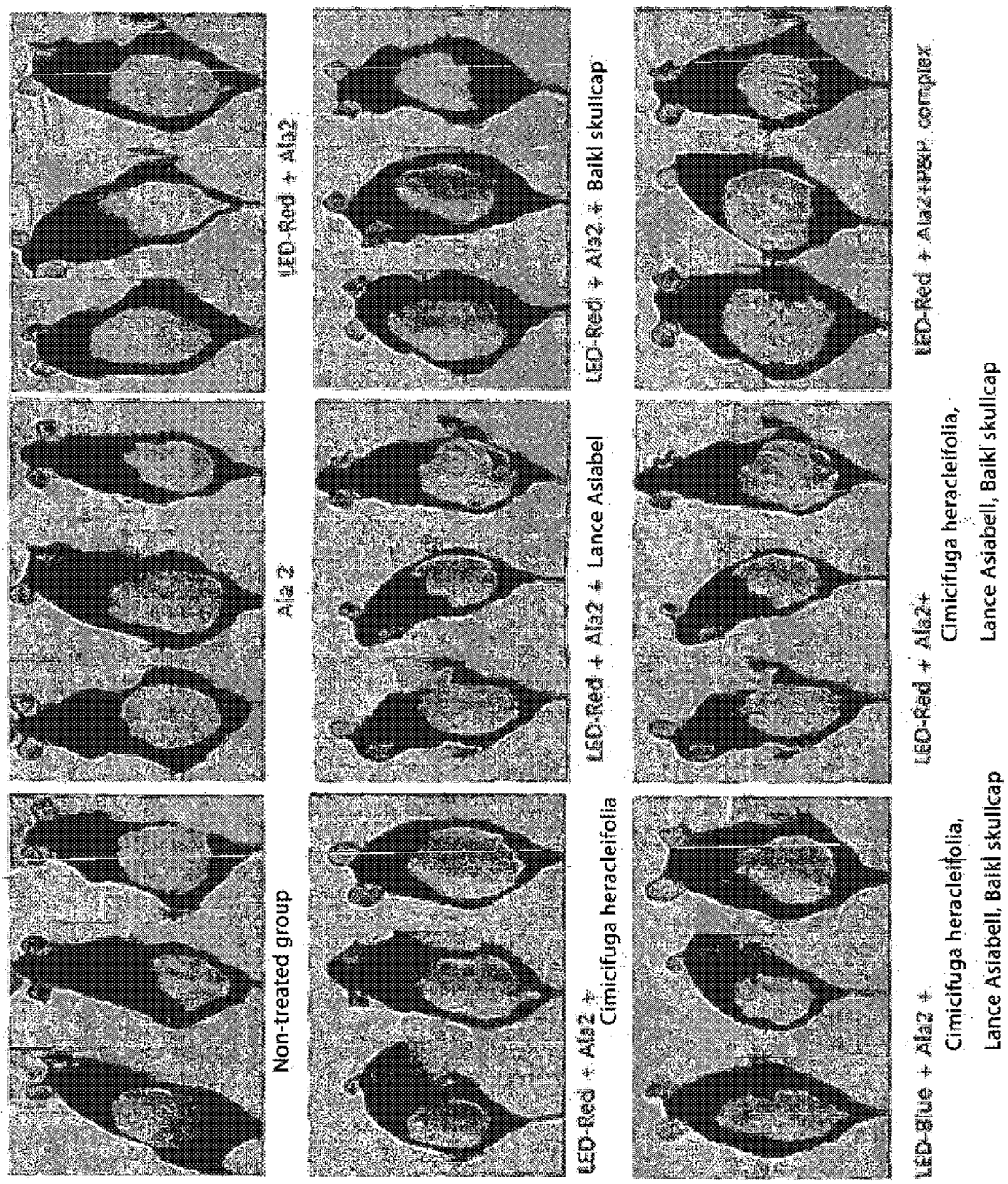
FIGS. 17 to 19 illustrate photographic results showing the hair growth promoting effects observed on day 3, day 5, and day 7 after sample treatment, respectively.
Figure 18:
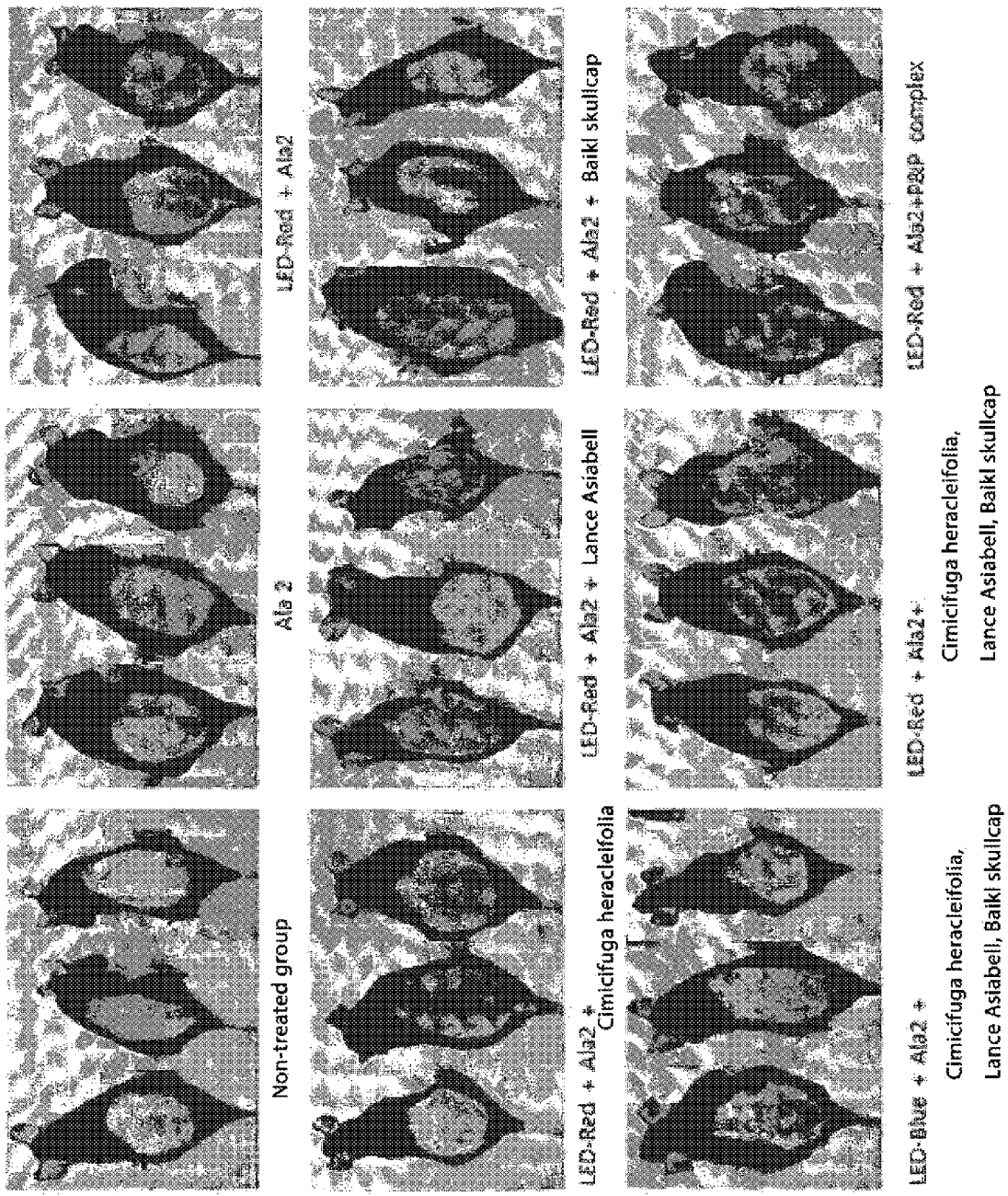
Figure 19:
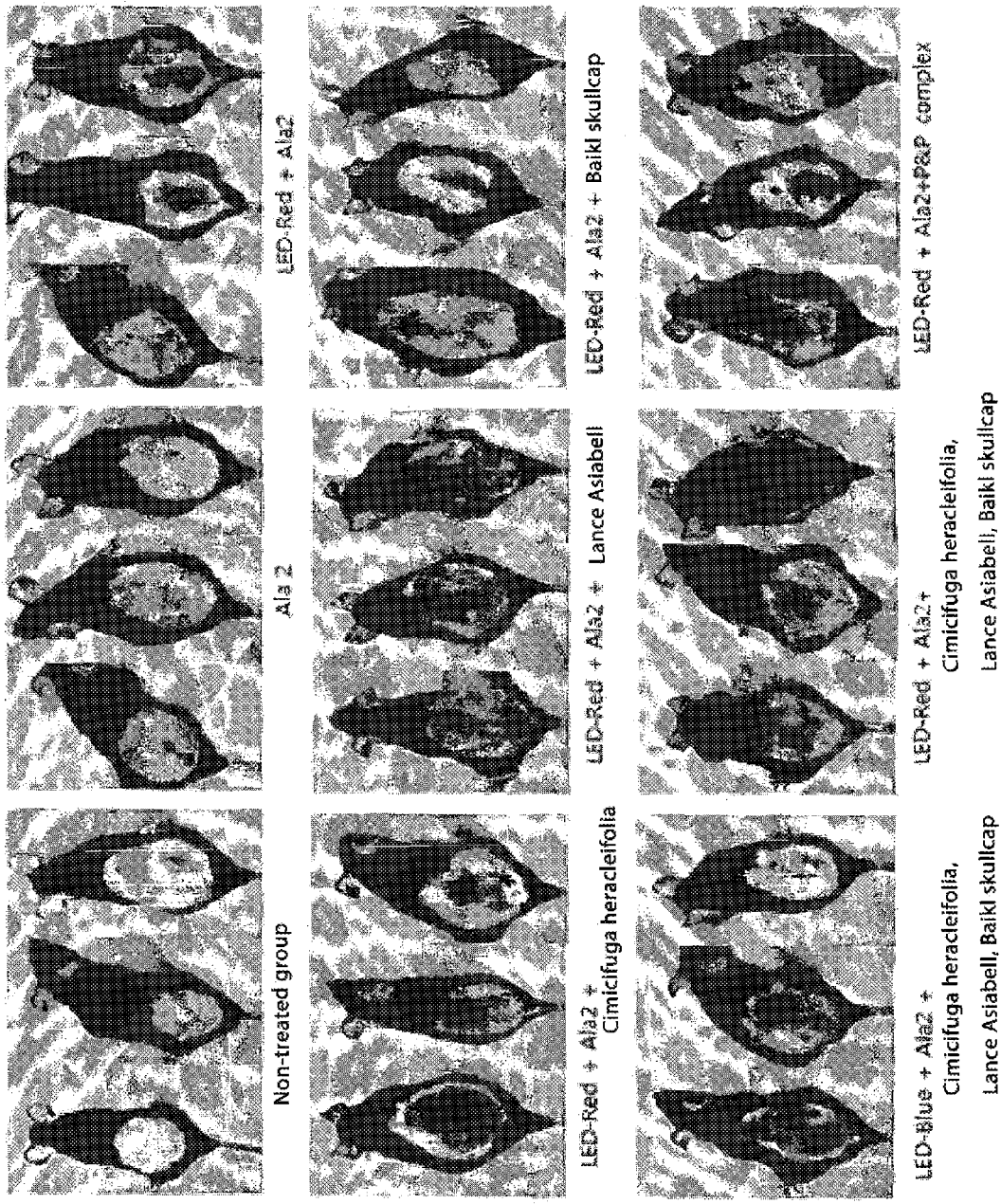

ALA-peptide treated group (see FIGS. 9 to 14). Interestingly, in the LED-Blue+ALA treated group, considerable hair loss phenomenon was observed compared to other treated groups on day 30 of observation (see FIG. 15).

Measurements of Hair Growth Promoting Effects Using a Mouse (Second Test)

A 7-week-old C57BL/6N mouse was used for this study, and hair of the mouse's back was completely removed using a wax at the age of 49 days to 51 days at which the C57BL/6N mouse enters catagen for the second time. In order to verify hair growth promoting effects of the test materials, it was treated once a day for 24 days. More particularly, the ALA and ALA-peptide were sprayed 3 times before LED radiation, and the LED treated groups were verified after treated for 5 minutes. Compositions of the test materials for this test are shown in Table 2 below.

TABLE 2

Treatment compositions of test materials of second test group

| No. | Treatment material |
|---|---|
| 1 | Untreated (control group) |
| 2 | ALA-peptide |
| 3 | LED-Red + ALA-peptide |
| 4 | LED-Red + ALA-peptide + *Cimicifuga heracleifolia* |
| 5 | LED-Red + ALA-peptide + Lance Asiabell |
| 6 | LED-Red + ALA-peptide + Baikl skullcap |
| 7 | LED-Red + ALA-peptide + *Cimicifuga heracleifolia* + Lance Asiabell + Baikl skullcap |
| 8 | LED-Blue + ALA-peptide + *Cimicifuga heracleifolia* + Lance Asiabell + Baikl skullcap |
| 9 | LED-Red + ALA-peptide + P&P complex |

As a result of testing the hair growth effects using the mouse, there were little differences in hair growth levels in an untreated group and an ALA-peptide treated group (see FIGS. 16 to 19).

Figure 20A:
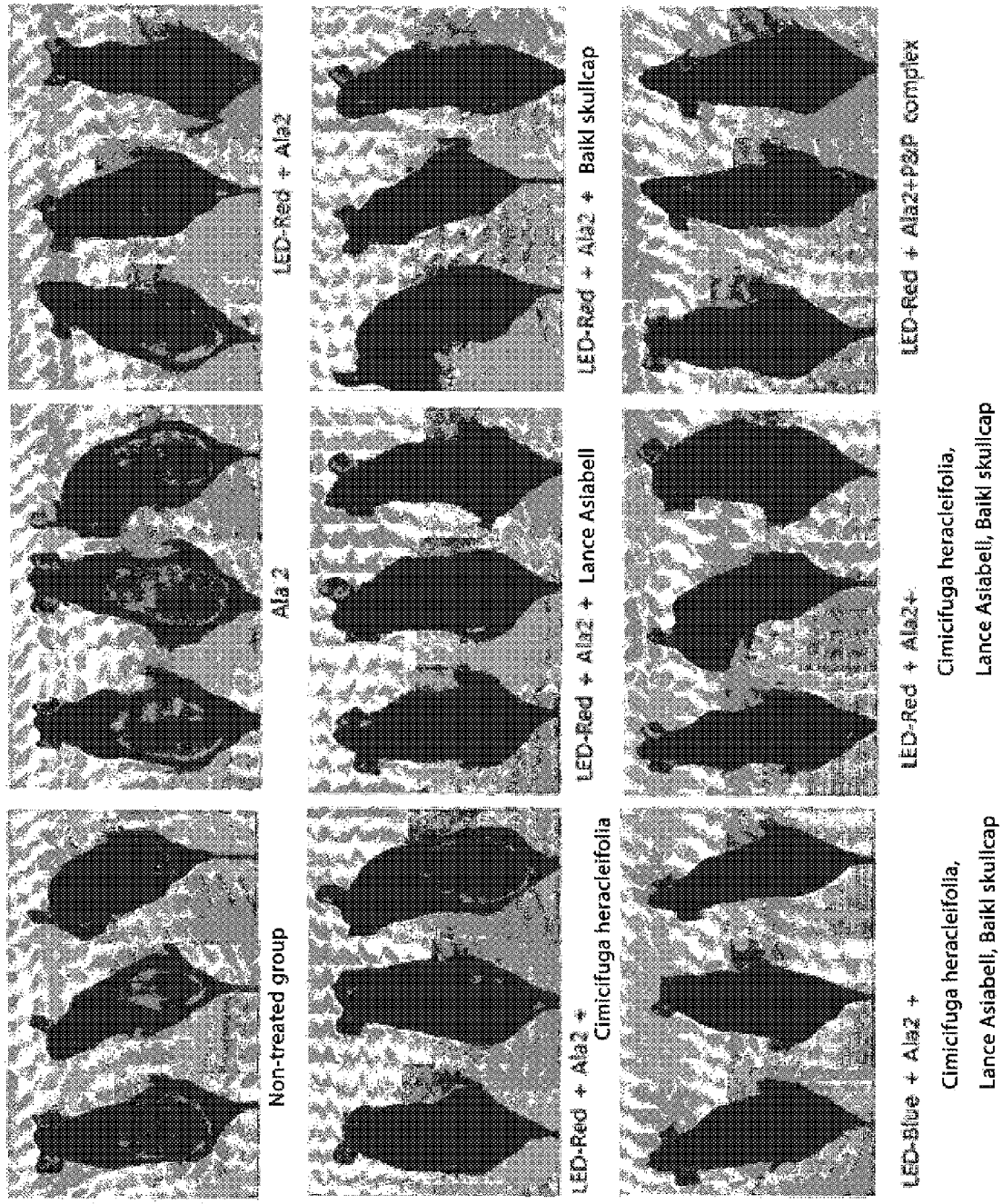
FIG. 20A illustrates photographs showing the hair growth promoting effects of the treated samples compared to an untreated group.
Figure 20B:
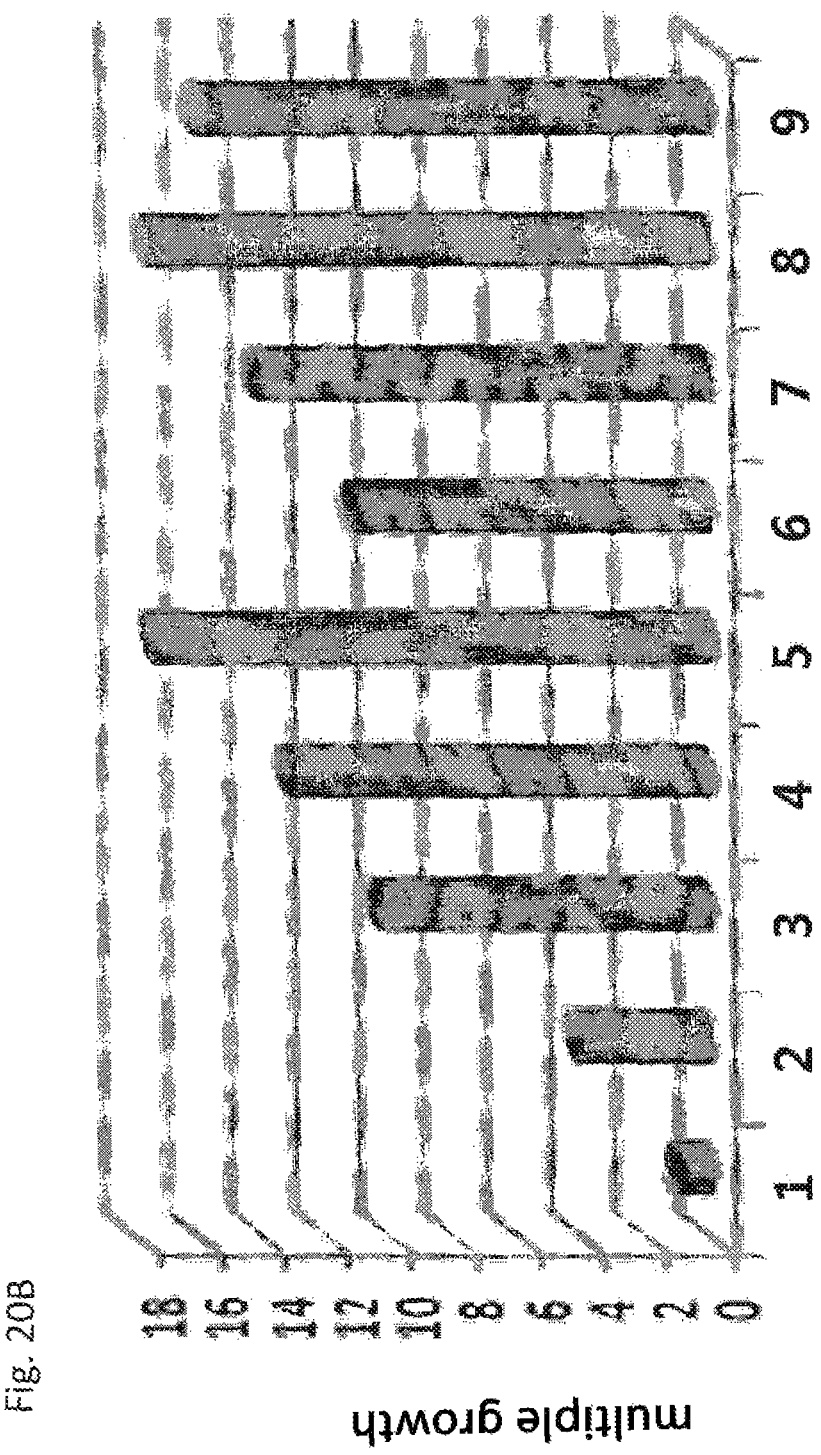
FIG. 20B illustrates a graph showing a result quantifying the hair growth promoting effects of the treated samples compared to an untreated group. Notation: lane 1, an untreated group; lane 2, ALA-peptide (Ala2); lane 3, LED-Red-Ala2; lane 4, LED-Red-Ala2+*Cimicifuga heracleifolia* (1 mg/ml); lane 5, LED-Red-Ala2+Lance Asiabell (1 mg/ml); lane 6, LED-Red-Ala2+Baikl skullcap (1 mg/ml); lane 7, LED-Blue-Ala2+*Cimicifuga heracleifolia*+Lance Asiabell+Baikl skullcap; lane 8, LED-Red-Ala2+*Cimicifuga heracleifolia*+Lance Asiabell+Baikl skullcap; and lane 9, LED-Red-Ala2+P&P complex.
Figure 20C:
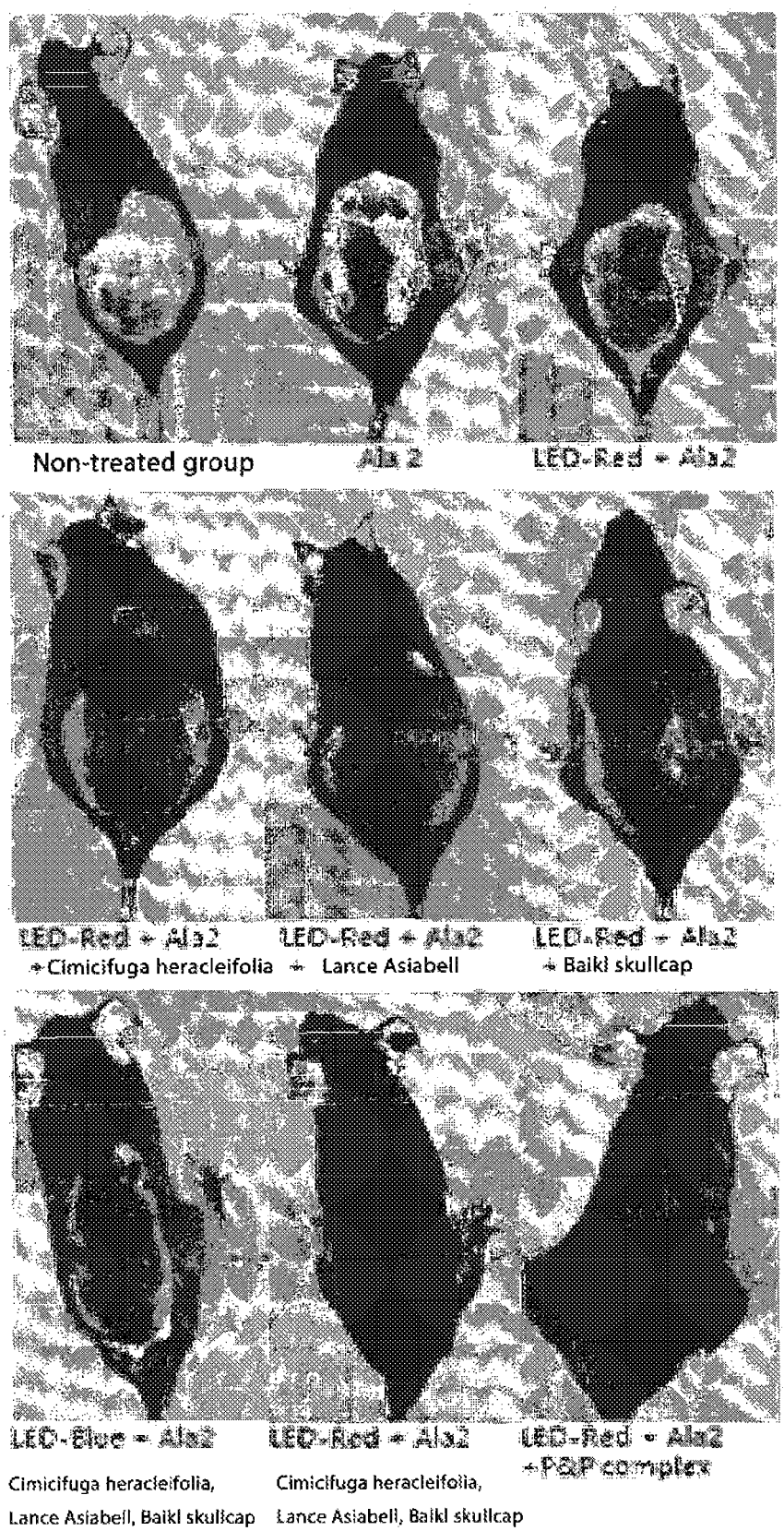
FIG. 20C illustrates photographic results showing the hair growth promoting effects observed on 9 days compared to an untreated group.
Figure 21:
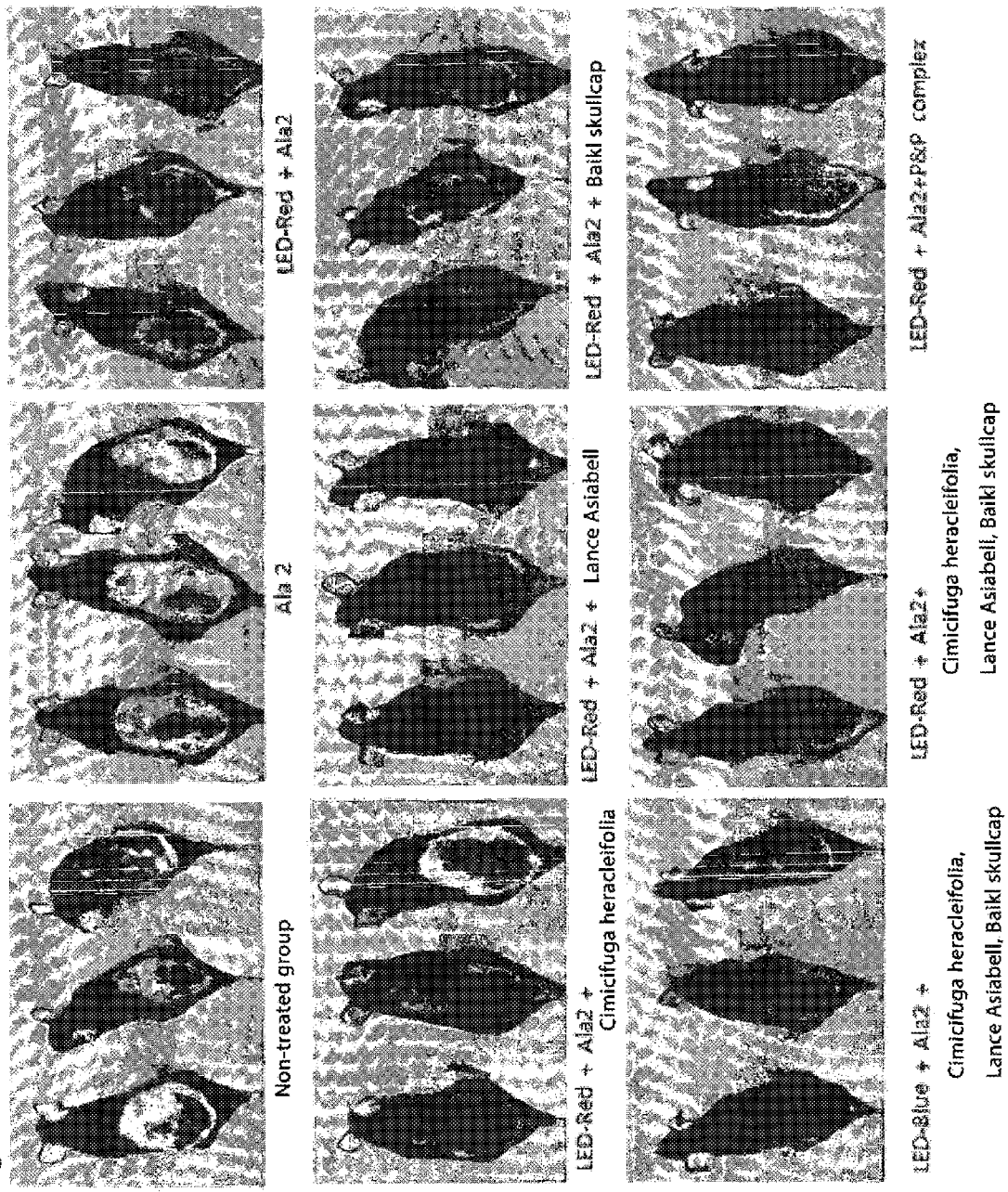
Figure 22:
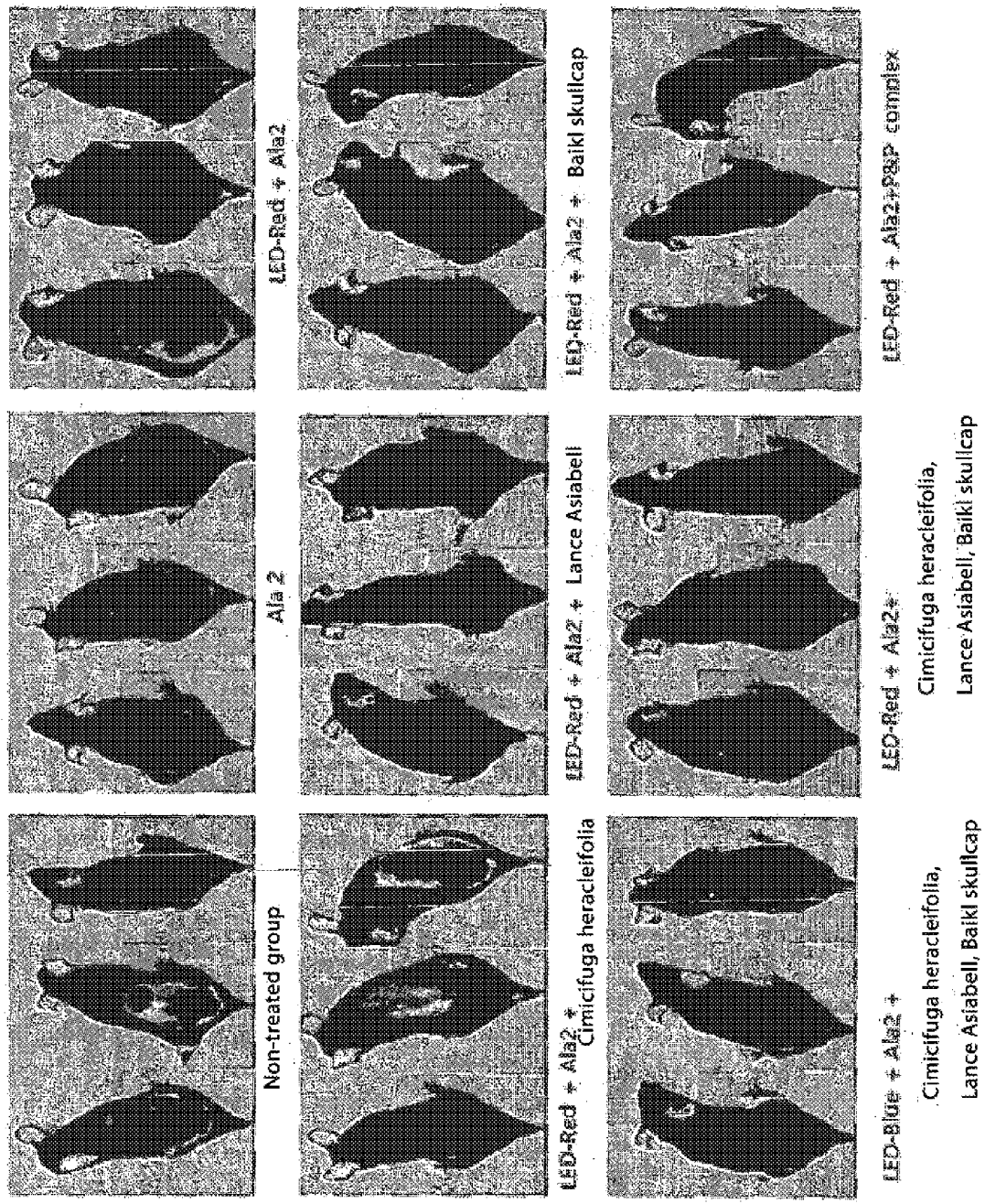
Figure 23:
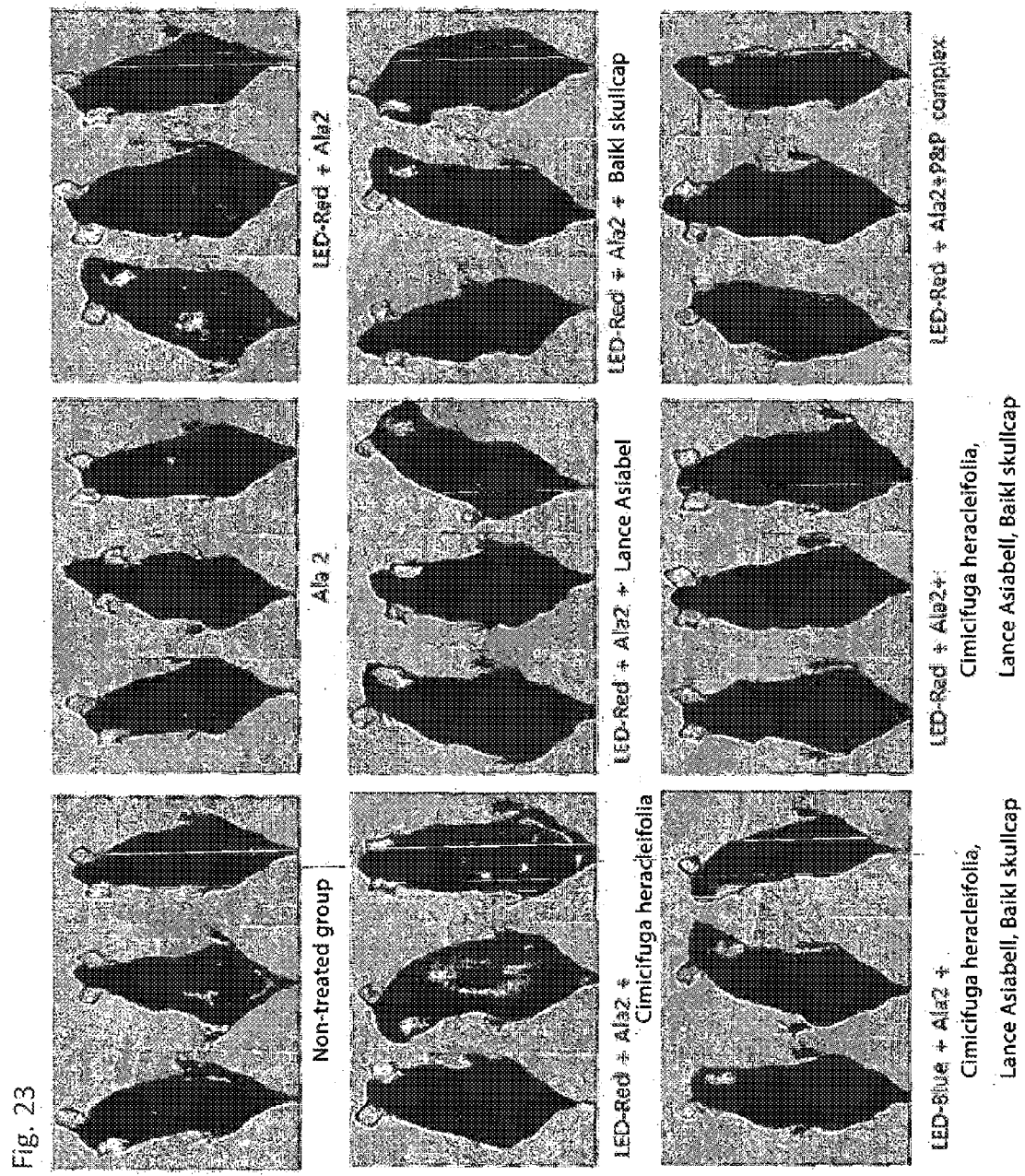

In contrast, in LED-Red+ALA-peptide, LED-Red+ALA-peptide+*Cimicifuga heracleifolia* extracts (1 mg/ml), LED-Red+ALA-peptide+Lance Asiabell extracts (1 mg/ml), LED-Red+ALA-peptide+Baikl skullcap extracts (1 mg/ml), LED-Red+ALA-peptide+*Cimicifuga heracleifolia*+Lance Asiabell+Baikl skullcap, LED-Blue+ALA-peptide+*Cimicifuga heracleifolia*+Lance Asiabell+Baikl skullcap, and LED-Red+ALA-peptide+P&P complex treated groups, increasing effects in the significant hair growth amounts due to hair growth promoting effects compared to the untreated group were observed. Particularly, in the LED-Red+ALA-peptide+Lance Asiabell, the LED-Red+ALA-peptide+*Cimicifuga heracleifolia*+Lance Asiabell+Baikl skullcap, the LED-Blue+ALA-peptide+*Cimicifuga heracleifolia*+Lance Asiabell+Baikl skullcap, and the LED-Red+ALA-peptide+P&P complex treated groups, a very great hair loss promoting effect was observed compared to other treated groups (see FIGS. 20A to 20C and 21). For example, on day 9 after sample treatment, in the LED-Red+ALA-peptide, the LED-Red+ALA-peptide+*Cimicifuga heracleifolia*, the LED-Red+ALA-peptide+Lance Asiabell, LED-Red+ALA-peptide+Baikl skullcap, the LED-Blue+ALA-peptide+*Cimicifuga heracleifolia*+Lance Asiabell+Baikl skullcap, the LED-Red+ALA-peptide+*Cimicifuga heracleifolia*+Lance Asiabell+Baikl skullcap, and the LED-Red+ALA-peptide+P&P complex treated groups, the significant hair growth promoting effects compared to the untreated group were observed. Above all, LED-Red+ALA-peptide+Lance Asiabell and LED-Red+ALA-peptide+*Cimicifuga heracleifolia*+Lance Asiabell+Baikl skullcap exhibited 18-fold or more hair growth promoting effects compared to the untreated group (see FIG. 20B).

While specific embodiments of the present invention were described in detail above, it will be apparent to one of ordinary skill in the art that these specific descriptions are only preferable implementations and the scope of the present invention is not limited to these. Accordingly, the practical scope of the present invention will be defined by the appended claims and the equivalent thereof.

The invention claimed is:

1. A composition for improving or promoting hair growth comprising:
    an active ingredient, wherein the active ingredient includes a peptide coupled to a photosensitizer (photosensitizer-peptide),
    wherein the photosensitizer is 5-aminolevulinic acid (ALA),
    wherein the peptide is glycine-histidine-lysine, and
    wherein the photosensitizer is activated by light-emitting diode (LED) radiation, wherein the LED radiation is a long wavelength of 650 to 675 nm.

2. The composition of claim 1, wherein an irradiation distance of the LED is within 2 to 10 cm.

3. The composition of claim 1, wherein the composition further comprises Cimicifuga *heracleifolia* extracts, Baikl skullcap extracts Lance Asiabell extracts, or combinations thereof.

\* \* \* \* \*